(12) United States Patent
Aviles et al.

(10) Patent No.: US 7,867,777 B2
(45) Date of Patent: *Jan. 11, 2011

(54) METHOD FOR OBTAINING SAMPLE MATERIAL

(75) Inventors: Robert C. Aviles, Merrimack, NH (US);
Mark A. Talmer, Pepperell, MA (US);
Gerard J. Sevigny, Nashua, NH (US);
Matthew W. Webb, Encinitas, CA (US);
Gus G. Tseo, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 68 days.

This patent is subject to a terminal disclaimer.

(21) Appl. No.: 11/554,394

(22) Filed: Oct. 30, 2006

(65) Prior Publication Data

US 2007/0054413 A1    Mar. 8, 2007

Related U.S. Application Data

(62) Division of application No. 10/439,456, filed on May 16, 2003, now Pat. No. 7,132,082.

(60) Provisional application No. 60/381,551, filed on May 17, 2002.

(51) Int. Cl.
*G01N 1/10* (2006.01)
(52) U.S. Cl. .......................... 436/180; 436/47; 436/48; 436/179; 422/65; 422/99; 422/102; 422/104
(58) Field of Classification Search ............ 422/62–66, 422/99, 102, 104; 436/47–49, 174, 176–180
See application file for complete search history.

(56) References Cited

U.S. PATENT DOCUMENTS

| 143,417 A | 10/1873 | Munroe |
| 418,940 A | 1/1890 | Bray |
| 1,168,535 A | 1/1916 | Moltrum |
| 1,549,111 A | 8/1925 | Grollman |

(Continued)

FOREIGN PATENT DOCUMENTS

EP    0 100 663 A2    2/1984

(Continued)

OTHER PUBLICATIONS

JPO Office Action, Japanese Patent Application No. 2004-504626, Aug. 29, 2008.

(Continued)

*Primary Examiner*—Jill Warden
*Assistant Examiner*—Dwayne K Handy
(74) *Attorney, Agent, or Firm*—Charles B. Cappellari

(57) ABSTRACT

A sample carrier comprising a frame and one or more sample tube receiving structures pivotally connected to the frame. Each sample tube receiving structure includes a bottom member adapted to receive a plurality of sample tubes and a top member having a plurality of aligned apertures sized to receive sample tubes therethrough. The sample tube receiving structures can be releasably locked relative to a support wall of the frame, thereby substantially immobilizing sample tubes that are held by the sample carrier.

17 Claims, 23 Drawing Sheets

U.S. PATENT DOCUMENTS

| | | | |
|---|---|---|---|
| 1,634,953 A | 7/1927 | McCune et al. |
| D110,691 S | 8/1938 | Dudley |
| 2,467,873 A | 4/1949 | Weir |
| 2,708,037 A | 5/1955 | Planeta |
| 2,741,913 A | 4/1956 | Dovas |
| 2,902,170 A | 9/1959 | Miller |
| 2,956,686 A | 10/1960 | Garey |
| 2,979,210 A | 4/1961 | Patterson |
| 3,072,362 A | 1/1963 | Allen |
| 3,109,084 A | 10/1963 | Walsh |
| 3,115,247 A | 12/1963 | Hauser |
| 3,142,385 A | 7/1964 | Kahlenberg |
| 3,175,695 A | 3/1965 | Goodman et al. |
| 3,186,556 A | 6/1965 | Forsstrom |
| 3,375,934 A | 4/1968 | Bates |
| 3,390,783 A | 7/1968 | Quackenbush, Jr. |
| 3,474,913 A | 10/1969 | Jungner et al. |
| D216,491 S | 1/1970 | Brown |
| 3,605,829 A | 9/1971 | Genese et al. |
| 3,643,812 A | 2/1972 | Mander et al. |
| 3,680,967 A | 8/1972 | Engelhardt |
| 3,698,563 A | 10/1972 | Gordon et al. |
| 3,744,661 A | 7/1973 | Fischer, Jr. |
| 3,752,651 A | 8/1973 | Bush |
| 3,765,538 A | 10/1973 | Kowert |
| 3,785,773 A | 1/1974 | Rohrbaugh |
| RE28,165 E | 9/1974 | McCormick |
| 3,904,035 A | 9/1975 | Metzler et al. |
| 3,905,482 A | 9/1975 | Knulst |
| 3,905,772 A | 9/1975 | Hartnett et al. |
| 3,909,203 A | 9/1975 | Young et al. |
| 3,960,271 A | 6/1976 | Nelson |
| 4,036,391 A | 7/1977 | Prodel |
| 4,043,762 A | 8/1977 | Olds |
| 4,055,396 A | 10/1977 | Meyer et al. |
| 4,124,122 A | 11/1978 | Emmitt |
| 4,160,803 A | 7/1979 | Potts |
| 4,202,634 A | 5/1980 | Kraft et al. |
| 4,207,289 A | 6/1980 | Weiss |
| 4,265,855 A | 5/1981 | Mandle et al. |
| 4,284,603 A | 8/1981 | Korom |
| 4,287,155 A | 9/1981 | Tersteeg et al. |
| 4,322,216 A | 3/1982 | Lillig et al. |
| D265,126 S | 6/1982 | Beall |
| 4,391,780 A | 7/1983 | Boris |
| 4,407,943 A | 10/1983 | Cole et al. |
| 4,422,555 A | 12/1983 | Jacobs |
| 4,434,890 A | 3/1984 | Sieck et al. |
| 4,438,068 A | 3/1984 | Forrest |
| 4,495,150 A | 1/1985 | Cook et al. |
| 4,510,119 A | 4/1985 | Hevey |
| 4,522,089 A | 6/1985 | Alvi |
| D280,130 S | 8/1985 | Harkins et al. |
| 4,534,465 A | 8/1985 | Rothermel et al. |
| D286,912 S | 11/1986 | Andersen |
| 4,639,135 A | 1/1987 | Borer et al. |
| D290,401 S | 6/1987 | Bjorkman |
| 4,751,052 A | 6/1988 | Schwartz et al. |
| 4,761,268 A | 8/1988 | Andersen et al. |
| 4,787,523 A | 11/1988 | Kalous |
| 4,805,772 A | 2/1989 | Shaw et al. |
| 4,824,641 A | 4/1989 | Williams |
| 4,849,177 A | 7/1989 | Jordan |
| 4,895,650 A | 1/1990 | Wang |
| 4,932,533 A | 6/1990 | Collier |
| 4,933,147 A | 6/1990 | Hollar et al. |
| 4,948,564 A | 8/1990 | Root et al. |
| 4,963,493 A | 10/1990 | Daftsios |
| 4,982,580 A | 1/1991 | Mears |
| 5,004,103 A | 4/1991 | Connors et al. |
| 5,006,066 A | 4/1991 | Rouse |
| 5,029,699 A | 7/1991 | Insley et al. |
| 5,057,282 A | 10/1991 | Linder |
| 5,077,013 A | 12/1991 | Guigan |
| 5,080,232 A | 1/1992 | Leoncavallo et al. |
| 5,082,631 A | 1/1992 | Lenmark, Sr. et al. |
| 5,098,663 A | 3/1992 | Berthold et al. |
| 5,108,287 A | 4/1992 | Yee et al. |
| 5,127,541 A | 7/1992 | Wakatake |
| 5,128,105 A | 7/1992 | Berthold et al. |
| 5,133,939 A | 7/1992 | Mahe |
| 5,137,693 A | 8/1992 | Mawhirt |
| 5,169,603 A | 12/1992 | Landsberger |
| 5,173,265 A | 12/1992 | Golias et al. |
| D333,522 S | 2/1993 | Gianino |
| 5,186,339 A | 2/1993 | Heissler |
| 5,191,975 A | 3/1993 | Pezzoli et al. |
| D336,219 S | 6/1993 | Held |
| 5,217,694 A | 6/1993 | Gibler et al. |
| 5,232,669 A | 8/1993 | Pardinas |
| 5,318,753 A | 6/1994 | Honda |
| 5,322,668 A | 6/1994 | Tomasso |
| 5,324,481 A | 6/1994 | Dunn et al. |
| 5,350,564 A | 9/1994 | Mazza et al. |
| 5,378,433 A | 1/1995 | Duckett et al. |
| 5,456,360 A | 10/1995 | Griffin |
| 5,456,882 A | 10/1995 | Covain |
| 5,472,669 A | 12/1995 | Miki et al. |
| 5,533,700 A | 7/1996 | Porter |
| 5,571,481 A | 11/1996 | Powell et al. |
| 5,579,928 A | 12/1996 | Anukwuem |
| 5,632,388 A | 5/1997 | Morrison et al. |
| 5,642,816 A | 7/1997 | Kelly et al. |
| 5,650,125 A | 7/1997 | Bosanquet |
| 5,651,941 A | 7/1997 | Stark et al. |
| 5,687,849 A | 11/1997 | Borenstein et al. |
| 5,700,429 A | 12/1997 | Buhler et al. |
| 5,704,495 A | 1/1998 | Bale et al. |
| 5,777,303 A | 7/1998 | Berney |
| D405,192 S | 2/1999 | Smith et al. |
| 5,876,926 A * | 3/1999 | Beecham ........................ 435/5 |
| 5,897,090 A | 4/1999 | Smith et al. |
| 5,916,527 A | 6/1999 | Haswell |
| 5,931,318 A | 8/1999 | Shauo |
| D413,677 S | 9/1999 | Dumitrescu et al. |
| D414,273 S | 9/1999 | Smith et al. |
| 5,959,221 A | 9/1999 | Boyd et al. |
| D417,009 S | 11/1999 | Boyd |
| 5,985,219 A | 11/1999 | Lind |
| 5,993,745 A | 11/1999 | Laska |
| 5,996,818 A | 12/1999 | Boje et al. |
| 6,015,534 A | 1/2000 | Atwood |
| D420,747 S | 2/2000 | Dumitrescu et al. |
| D421,130 S | 2/2000 | Cohen et al. |
| 6,027,691 A | 2/2000 | Watts et al. |
| 6,065,617 A | 5/2000 | Cohen et al. |
| 6,123,205 A | 9/2000 | Dumitrescu et al. |
| D433,759 S | 11/2000 | Mathis et al. |
| 6,156,275 A | 12/2000 | Dumitrescu et al. |
| 6,190,619 B1 | 2/2001 | Kilcoin et al. |
| 6,193,064 B1 | 2/2001 | Finneran |
| D439,673 S | 3/2001 | Brophy et al. |
| 6,221,317 B1 | 4/2001 | Carl |
| 6,235,245 B1 | 5/2001 | Sherman et al. |
| 6,274,092 B1 | 8/2001 | Itoh |
| 6,335,166 B1 | 1/2002 | Ammann et al. |
| 6,618,981 B1 | 9/2003 | Rodriguez |
| 2002/0021983 A1 | 2/2002 | Comte et al. |
| 2002/0108917 A1 | 8/2002 | Maruyama |
| 2003/0017084 A1 | 1/2003 | Dale et al. |

| | | | | |
|---|---|---|---|---|
| 2003/0215365 A1 | 11/2003 | Sevigny et al. | JP | 1-161154 | 6/1989 |
| | | | WO | WO93/01739 A1 | 2/1993 |

FOREIGN PATENT DOCUMENTS

| | | |
|---|---|---|
| EP | 0219802 A3 | 4/1987 |
| EP | 0919281 A2 | 6/1999 |
| EP | 0 965 385 A2 | 12/1999 |
| EP | 0965385 A2 | 12/1999 |

OTHER PUBLICATIONS

IPA Examination Report, Australian Patent Application No. 2003234594, Dec. 3, 2008.

* cited by examiner

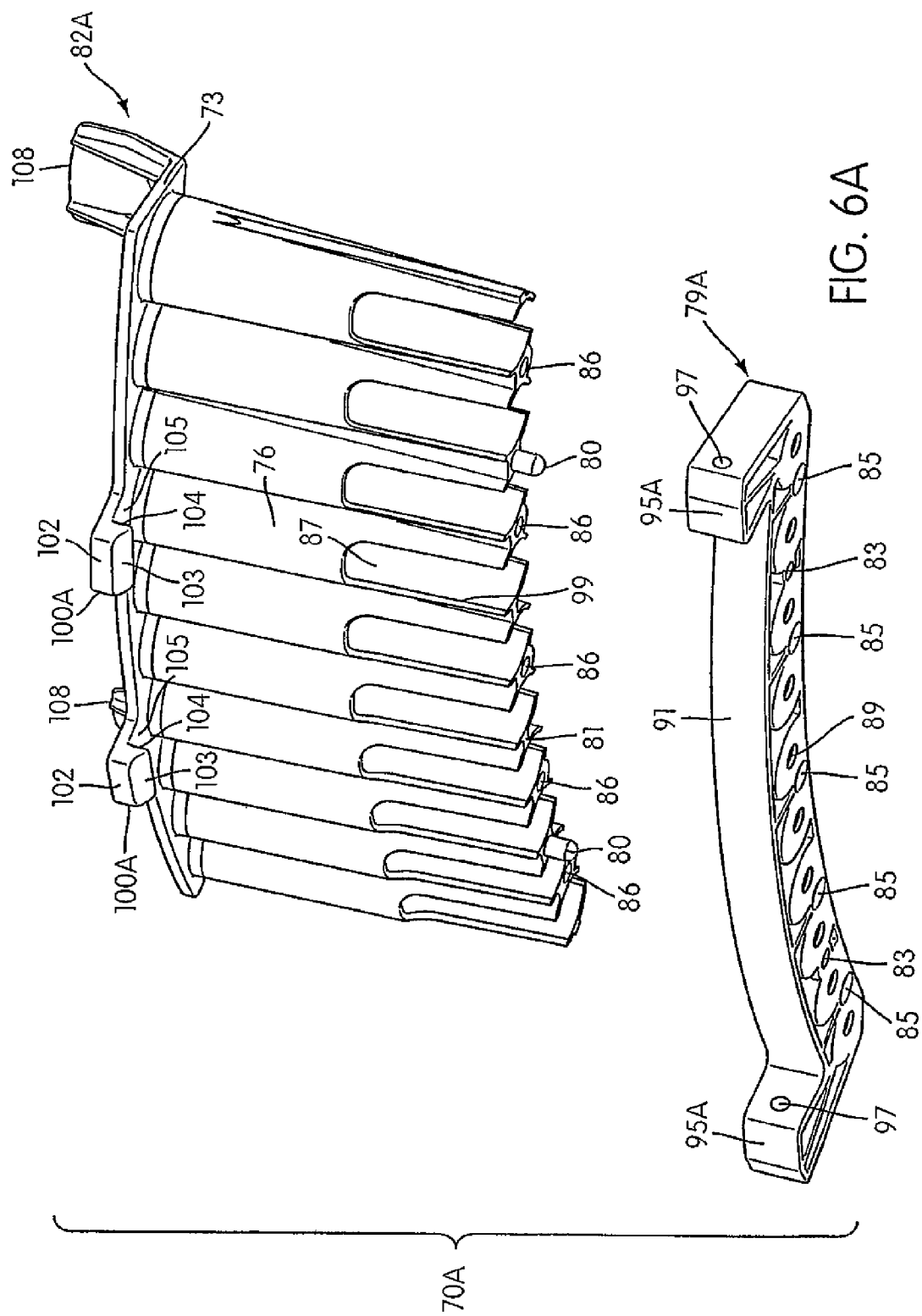

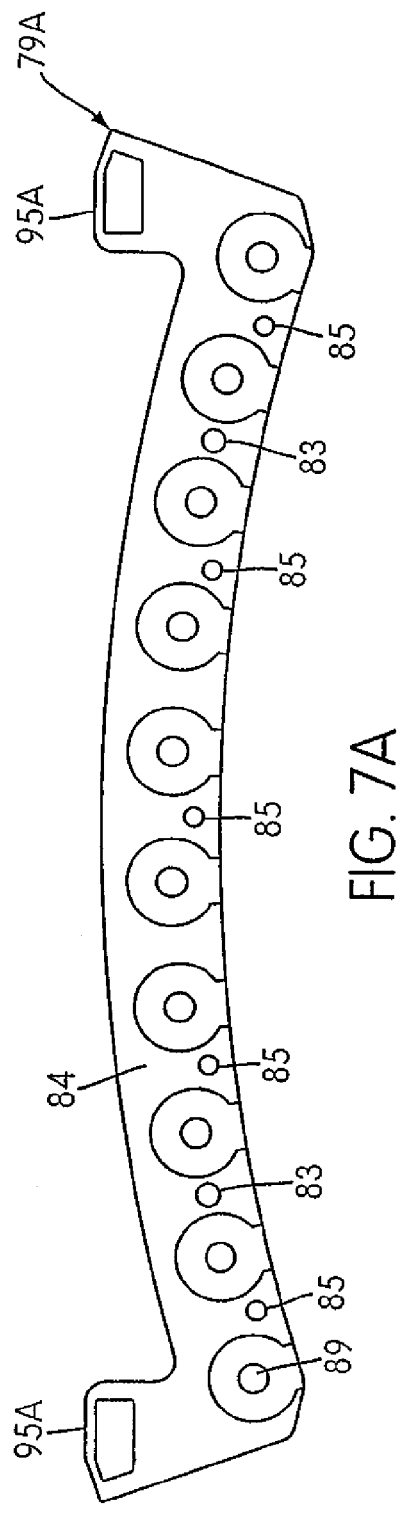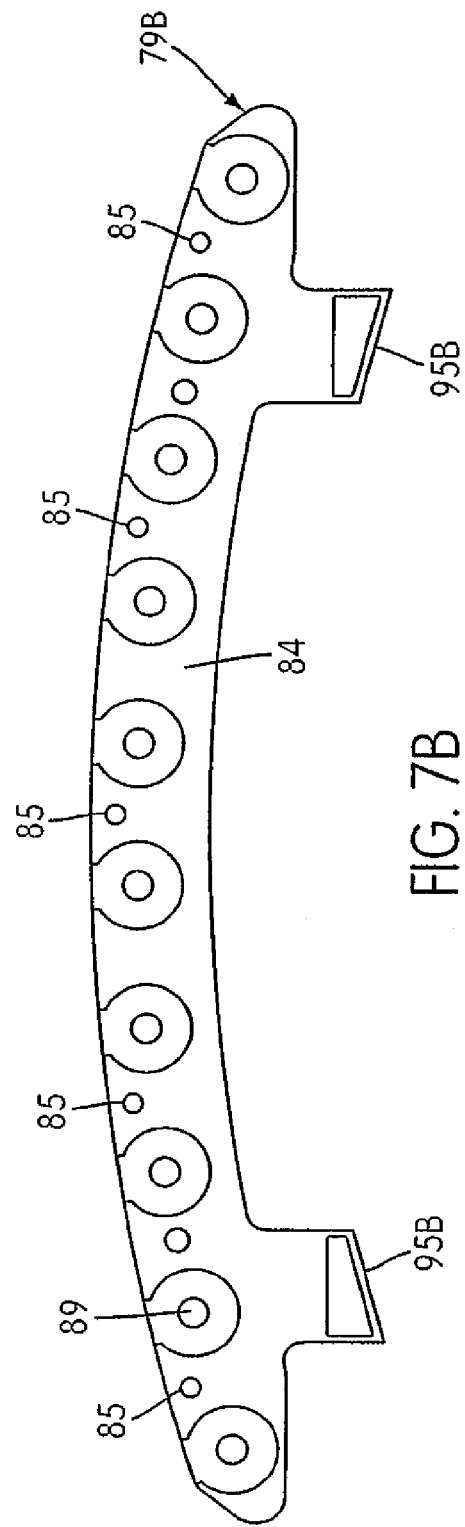
FIG. 7A
FIG. 7B

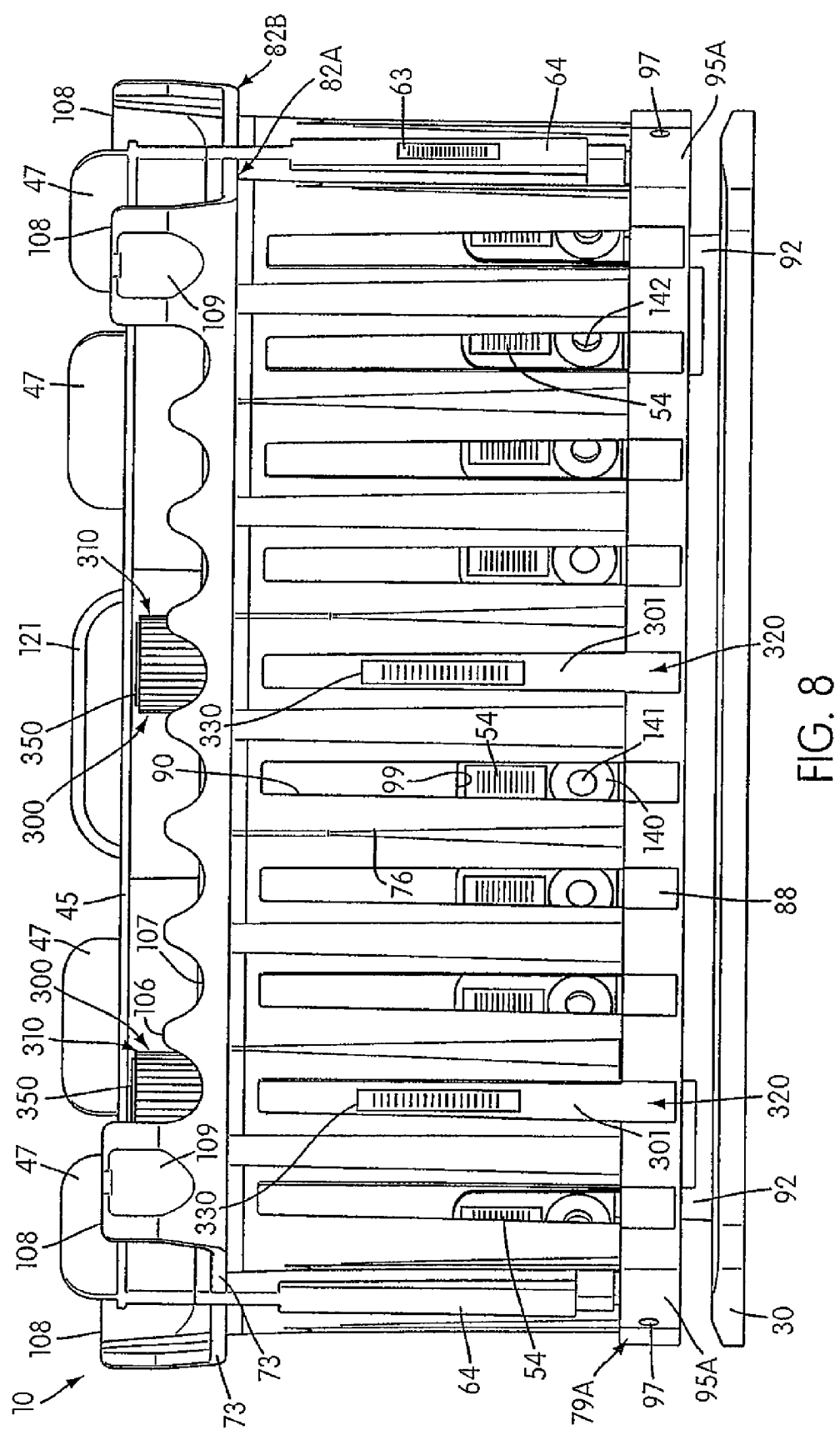

METHOD FOR OBTAINING SAMPLE MATERIAL

CROSS-REFERENCE TO RELATED APPLICATIONS

This application is a divisional of U.S. application Ser. No. 10/439,456, filed May 16, 2003, now U.S. Pat. No. 7,132,082, which claims the benefit of U.S. Provisional Application No. 60/381,551, filed May 17, 2002, the contents of each of which applications is hereby incorporated by reference herein.

FIELD OF THE INVENTION

The present invention relates to a sample carrier for receiving and immobilizing a plurality of sample tubes. The sample carrier of the present invention can be used in conjunction with an automated sampling system and is especially useful with sample tubes having penetrable caps. The present invention further relates to a method for obtaining a test sample from a sample tube which is immobilized in a sample carrier. The method of the present invention is particularly suited for use with sample tubes having penetrable caps.

INCORPORATION BY REFERENCE

All references referred to herein are hereby incorporated by reference in their entirety. The incorporation of these references, standing alone, should not be construed as an assertion or admission by the inventors that any portion of the contents of all of these references, or any particular reference, is considered to be essential material for satisfying any national or regional statutory disclosure requirement for patent applications. Notwithstanding, the inventors reserve the right to rely upon any of such references, where appropriate, for providing material deemed essential to the claimed invention by an examining authority or court. No reference referred to herein is admitted to be prior art to the claimed invention.

BACKGROUND OF THE INVENTION

Procedures for determining the presence or absence of specific organisms or viruses in a test sample commonly rely upon nucleic acid-based probe testing. To increase the sensitivity of these tests, an amplification step is often included to increase the number of potential nucleic acid target sequences present in the test sample. There are many procedures for amplifying nucleic acids which are well known in the art, including, but not limited to, the polymerase chain reaction (PCR), (see, e.g., Mullis, "Process for Amplifying, Detecting, and/or Cloning Nucleic Acid Sequences," U.S. Pat. No. 4,683,195), transcription-mediated amplification (TMA), (see, e.g., Kacian et al., "Nucleic Acid Sequence Amplification Methods," U.S. Pat. No. 5,399,491), ligase chain reaction (LCR), (see, e.g., Birkenmeyer, "Amplification of Target Nucleic Acids Using Gap Filling Ligase Chain Reaction," U.S. Pat. No. 5,427,930), and strand displacement amplification (SDA), (see, e.g., Walker, "Strand Displacement Amplification," U.S. Pat. No. 5,455,166). A review of several amplification procedures currently in use, including PCR and TMA, is provided in HELEN H. LEE ET AL., NUCLEIC ACID AMPLIFICATION TECHNOLOGIES (1997).

Amplification, however, raises concerns about cross-contamination, since transferring even a minute amount of target-containing sample to a target-negative sample could lead to the production of billions of target sequences in the "negative" sample, possibly resulting in a false-positive that might otherwise have been negative in the absence of an amplification step. The source of a contaminating sample transfer may be an aerosol or bubbles released from the sample tube of a sample collection kit when a cap component of the sample tube is removed by a practitioner. To minimize such sources of contamination, it would be desirable to have a sample carrier capable of substantially immobilizing sample tubes having penetrable caps which are designed and constructed to limit the release of an aerosol or bubbles when penetrated by a standard positive displacement pipette tip. Penetrable caps designed and constructed to limit the release of potentially contaminating material are disclosed by Anderson et al., "Collection Device and Method for Removing a Fluid Substance from the Same," U.S. Patent Application Publication No. US 2001-0041336 A1, and Kacian et al., "Penetrable Cap," U.S. Application Publication No. US 2002-0127147 A1.

By securely immobilizing sample tubes in a sample carrier, the sample tubes can be centered in an automated sampling system so that sample tubes can be sequentially penetrated by distinct pipette tips and air from within the sample tubes can be vented and filtered as the pipette tips enter the sample tubes. Moreover, if properly centered, the aerosol and bubble barriers of these penetrable caps can also function to remove sample residue from the outside of these pipette tips as they are being withdrawn from the sample tubes.

To secure sample tubes outfitted with penetrable caps in a sample carrier, the sample carrier must exert sufficient force against the sample tubes to prevent them from being extracted from the sample carrier during sampling, especially in automated sampling procedures where manual restraint of the sample tubes is not possible. The force exerted against the sample tubes, known as the "retaining force," may be supplied by leaf springs, for example, which are oriented so that the springs are biased against the sample tubes as they are inserted into the sample carrier. Sample carriers incorporating leaf springs are disclosed by, for example, Dale et al., "Sample Carrier and Drip Shield for Use Therewith," U.S. Patent Application Publication No. US 2003-0017084 A1. The force required to retain any given sample tube in a sample carrier during sampling will largely depend upon the withdrawal force. The "withdrawal force" is the upward force required to fully remove a fluid transfer device (e.g., pipette tip) from the sample tube after the cap component has been penetrated. As the withdrawal force increases, the retaining force must likewise increase. And the greater the retaining force, the more force practitioners must exert to insert sample tubes into conventional sample carriers, making the sample carriers more difficult to control and exposing practitioners to possible repetitive motion injuries, such as carpal tunnel syndrome.

Thus, a need exists for a sample carrier which provides an adequate retaining force for maintaining sample tubes in the sample carrier during sampling, while at the same time minimizing the force required to insert sample tubes into the sample carrier. Ideally, the sample carrier would be configured for use with an automated sampling device and would include means for centering the cap component under the sampling device. Secondary or failsafe means for retaining sample tubes in the sample carrier would also be desirable.

SUMMARY OF THE INVENTION

The present invention addresses the retaining force problems associated with conventional sample carriers by providing a sample carrier which comprises: (i) a frame which includes a base and a support wall joined to the base; and (ii) one or more sample tube receiving structures positioned above the base and adjacent the support wall, where each sample tube receiving structure includes a bottom member adapted to receive a plurality of sample tubes and a top member in fixed relationship above the bottom member, where the top member includes a plurality of aligned apertures, each aperture being sized to receive a sample tube therethrough. As used herein, the term "joined" means that the referred to components are directly or indirectly connected to each other, as through intervening structure. The sample tube receiving structures are pivotally connected to the frame, and the support wall and the sample tube receiving structures include means for releasably locking the sample tube receiving structures relative to the support wall. The sample carrier may be of any shape, but is preferably arcuately shaped for conforming use on an automated sample carousel.

In a preferred embodiment of the present invention, the sample carrier includes a pair of the sample tube receiving structures separated by the support wall. The apertures present in the top member of each sample tube receiving structure may be of any shape but preferably have a generally circular geometry. The size of the apertures may be the same or different to accommodate sample tubes which include caps having the same or different dimensions. Notwithstanding, the apertures preferably have the same dimensions and are equidistantly spaced on the top member of each sample tube receiving structure. The surface of the top member surrounding each aperture is preferably chamfered to facilitate the loading of sample tubes into the sample tube receiving areas.

In another embodiment of the present invention, one or more hinges are provided which join each sample tube receiving structure to the frame, thereby permitting the sample tube receiving structures to pivot relative to the frame. As used herein, the term "hinge" is given its ordinary meaning, and refers to a jointed or flexible device that allows the pivoting of a part on a stationary frame. Each hinge preferably includes a hinge point and a hinge clasp joining the base of the frame and the bottom member of the sample tube receiving structures, respectively. The hinge point extends upward from a top surface of the base and has a fixed and generally transversely oriented pin extending therethrough. Each hinge clasp extends inward from the bottom member of one of the sample tube receiving structures and comprises a side wall having a through-hole sized to receive an end of the pin, where the hinge clasp is constructed and arranged to permit the sample tube receiving structure to pivot relative to the support wall when the pin is inserted into the through-hole. Preferred sample carriers include two hinges, where the through-hole of each hinge clasp of each sample tube receiving structure has an end of a different pin inserted therein. When the sample carrier includes two sample tube receiving structures separated by the support wall, it is preferred that outer ends of the pins are fitted into the through-holes of the hinge clasps associated with one of the sample tube receiving structures and inner ends of the pins are fitted into the through-holes of the hinge clasps associated with the other sample tube receiving structure. In this way, the sample tube receiving structures can pivot independently relative to the frame.

In still another embodiment of the present invention, the sample carrier includes a latch comprising: (i) a handle; (ii) one or more first registration elements corresponding to and engaged by one or more second registration elements present in or contained on a top surface of the support wall positioned below and spaced-apart from the top wall, where the first and second registration elements are constructed and arranged to permit downward movement of the handle, and where the top wall has a slot positioned above the top surface of the support wall and through which at least a portion of the handle extends when the top wall is joined to the support wall; and (iii) a transverse structure interposed between and connecting the handle and the first registration elements, where the transverse structure and opposed inner walls of the support wall are constructed and arranged so that the transverse structure is in sliding engagement with the support wall. As used herein, the term "handle" is given its ordinary meaning, and refers to a part that is designed to be operated with the hand. In this embodiment, one or more clasps are also included which extend from a surface of each sample tube receiving structure opposed to the support wall, where each clasp is constructed and arranged to operatively engage the transverse structure, so that the latch is forced downward as the sample tube receiving structures are pivoted inward toward the support wall, and where the clasps and the transverse structure assume an interlocking relationship when the sample tube receiving structures obtain substantially parallel orientations relative to the support wall. In a preferred mode, the transverse structure includes extensions or tabs which fit into corresponding slots in the opposed inner walls of the support wall which permit sliding of the transverse structure relative to the support wall.

The first and second registration elements preferably comprise a pair of guide rods and corresponding holes in the top surface of the support wall, respectively. The guide rods depend from the transverse structure and a coil spring is disposed on each guide rod between a bottom surface of the transverse structure and the top surface of the support wall when the top wall is joined to the support wall. The holes in the support wall are constructed and arranged to receive distal ends of the guide rods in sliding engagement therein when the top wall is joined to the support wall.

Each sample tube receiving structure of the sample carrier preferably includes a pair of clasps. In a particularly preferred mode, each clasp extends inwardly from the top member and has a flat top surface and a downwardly sloped bottom surface, where the sloped bottom surface terminates substantially at a vertical surface depending from a flat bottom surface of each clasp, and where the sloped bottom surfaces are pivotally aligned with beveled sections of a top surface of the transverse structure opposite recesses in the transverse structure which are configured to accommodate the clasps when the vertical surfaces of the clasps are in touching contact with opposed inner surfaces of the recesses, thereby locking the sample tube receiving structures in substantially parallel orientations relative to the support wall.

In a yet another embodiment of the present invention, the top member of each sample tube receiving structure includes an upwardly extending outer edge to facilitate handling of the sample carrier and to minimize user contact with sample tubes provided to the sample carrier. Rather than having a strictly vertical orientation, the outer edge of this embodiment preferably flares upward from the top member. In this embodiment, the outer edge preferably includes a plurality of recesses, giving the outer edge a scalloped appearance, where each recess is positioned adjacent one of the apertures to provide access to and to facilitate manual manipulation of the sample tubes.

In further embodiment of the present invention, the support wall includes one or more springs, where each spring extends outward from a side wall of the support wall adjacent one of the sample tube receiving structures. As used herein, the term "spring" is given its ordinary meaning, and refers to an elastic device which regains its original shape after being compressed. Examples of springs that may be used with the present invention include leaf springs, coil springs and rubbers. Particularly preferred is a rubber which resists degradation by acids and bleaches, such as Viton®. Such rubbers are preferred because the sample carriers may exposed to acidic reagents and bleaches for killing microorganisms or degrading nucleic acid after performing a nucleic acid probe-based assay. If leaf springs are used, then surfaces of the springs may be chemically or physically altered to increase the coefficient of friction between the springs and outer surfaces of the sample tubes. Springs contemplated by the present invention are configured and arranged to be biased against sample tubes present in the sample tube receiving areas when the sample tube receiving structures are locked relative to the support wall. A separate spring is preferably associated with each sample tube receiving area. The sample tube retaining force of each spring of the present invention is preferably at least about 3 pounds force (13.34 N).

In a still a further embodiment of the present invention, the sample carriers comprise a plurality of sleeves, where each sleeve at least partially circumscribes one of the apertures in the top member of one of the sample tube receiving structures and depends from a bottom surface of the top member to a top surface of the bottom member. Each sleeve is dimensioned to receive a sample tube therein. Additionally, each sleeve has an opening formed therein which is dimensioned to receive at least a portion of one of the springs therethrough when the sample tube receiving structures are locked relative to the support wall. In a preferred mode, a distinct spring is positioned adjacent each opening in each sleeve.

Each sleeve of the present invention preferably includes a slot formed therein which is constructed and arranged to permit viewing or scanning of a machine readable label, such as a bar code, affixed to an inserted sample tube. The label may convey information about the source of a test sample or, by way of example, it may instruct an automated test instrument to perform a particular assay protocol on the test sample. In addition, the slot formed in each sleeve and a corresponding opening formed for receiving an adjacent spring therethrough may be configured and aligned to permit viewing or scanning of a machine readable label affixed to a side wall of the support wall above the adjacent spring when a sample tube is not present in a sleeve, thereby providing information about the presence or absence of a sample tube in the corresponding sample tube receiving area.

In yet a further embodiment of the present invention, the sample carrier further comprises a top wall which is joined to the support wall. The top wall extends laterally and overhangs each aperture in the top member of each sample tube receiving structure. The overhangs function as fail safes when the sample tube receiving structures are locked relative to the support wall by limiting the vertical distance that sample tubes can be unintentionally withdrawn from sample tube receiving areas. Bottom surfaces of the overhangs are vertically higher than top surfaces of sample tubes inserted into the sample tube receiving areas so that the sample tube receiving structures can be locked relative to the support wall.

In another embodiment of the present invention, the sample carrier further comprises one or more fins extending upward from the top wall for maintaining the sample carrier under a drip shield when an automated pipettor withdraws a pipette tip from a sample tube present in one of the sample tube receiving areas. In this embodiment, an automated sample carousel may advance the sample carrier under a drip shield having holes formed therein for accessing sample tubes present in a sample carrier. As used herein, a "drip shield" is any canopy-like structure under which a sample carrier may be conveyed and which includes through-holes for accessing sample tubes with a robotic pipettor, where the drip shield is constructed and arranged to limit carryover contamination between sample tubes present in the sample carrier. An example of a drip shield is disclosed by Ammann et al., "Automated Process for Isolating and Amplifying a Target Nucleic Acid Sequence," U.S. Pat. No. 6,335,166. In a preferred mode, the fin or fins are longitudinally or arcuately centered on the top wall and a top surface of the fin or fins are operatively positioned near a bottom surface of the drip shield, preferably about 0.125 inches (3.18 mm) below the bottom surface of the drip shield. The distance between the bottom surface of the drip shield and the top surface of the fin or fins should be less than the depth of a well or other holding structure for maintaining the sample carrier on a sample carousel or other conveying means. This is so that a sample carrier cannot be removed from the well or other holding structure should the penetrable components of a sample tube bind a pipette tip as it is being withdrawn from the sample tube. When the fin or fins make contact with the drip shield, the force that the drip shield exerts against the sample carrier should be sufficient to release the pipette tip from the sample tube so that the sample carrier remains in its holding structure.

In still another embodiment of the present invention, each aperture is dimensioned, and each associated sample tube receiving area is configured, so that a fully inserted sample tube is substantially immobilized. Immobilization of sample tubes is important since, in a preferred mode, the sample tubes include penetrable caps which are pierced by, for example, conventional plastic pipette tips before test sample is withdrawn from the sample tubes. Centering the pipette tips prior to puncturing the caps helps to limit the forces required to pierce the caps and can provide for more accurate pipetting. In a preferred embodiment, the sample tubes are centered for cap piercing to within about 0.125 inches (3.18 mm) from the longitudinal axis of a top surface of the cap component of the sample tube and more preferably to within about 0.1 inches (2.54 mm).

In a yet another embodiment of the present invention, the sample carrier includes a surface for affixing a machine readable label which provides information about the sample carrier, such as the source or type of test samples being carried or particular assays to be performed on each of the test samples. The surface for affixing the machine readable label is preferably a lateral end wall of the support wall. The label may include a scannable bar code or other machine readable information.

In a further embodiment of the present invention, a method is provided for obtaining at least a portion of a test sample from a sample tube, where the method comprises the steps of: (i) inserting a sample tube into a sample carrier adapted to receive the sample tube therein; (ii) applying a retaining force against the sample tube after the inserting step to substantially immobilize the sample tube in the sample carrier; and (iii) withdrawing at least a portion of a test sample from the sample tube, where the sample tube remains in the sample carrier during the withdrawing step. In a preferred mode, the inserting step can be accomplished by gravitation force, as the sample tube can be dropped or slid into an area of the sample carrier adapted to receive the sample tube therein, and the applying step provides a retaining force of at least about 3 pounds force (13.34 N). The applying step can include a change in the orientation of the sample tube in the sample carrier, and the retaining force is preferably applied by a spring joined to the sample carrier. In another preferred mode, the withdrawing step includes penetrating a surface of a cap component of the sample tube with a pipette tip. That portion of the test sample withdrawn from the sample tube may then be subjected to an assay protocol. The assay protocol may be any chemical, biochemical or biological test which is intended to provide information about the test sample or a constituent of the test sample. In a particularly preferred mode, the assay protocol includes performing a procedure for amplifying a nucleic acid sequence contained in a nucleic acid which may be present in the test sample.

These and other features, aspects, and advantages of the present invention will become apparent to those skilled in the art after considering the following detailed description, appended claims and accompanying drawings.

BRIEF DESCRIPTION OF THE DRAWINGS

FIGS. 6A and 6B are exploded perspective views of the sample tube receiving structures of FIGS. 4A and 4B, respectively.

FIGS. 7A and 7B are top views of the bottom members of the sample tube receiving structures of FIGS. 4A and 4B, respectively.

FIG. 8 is a front view of the assembled sample carrier of FIG. 1.

Figure 1:
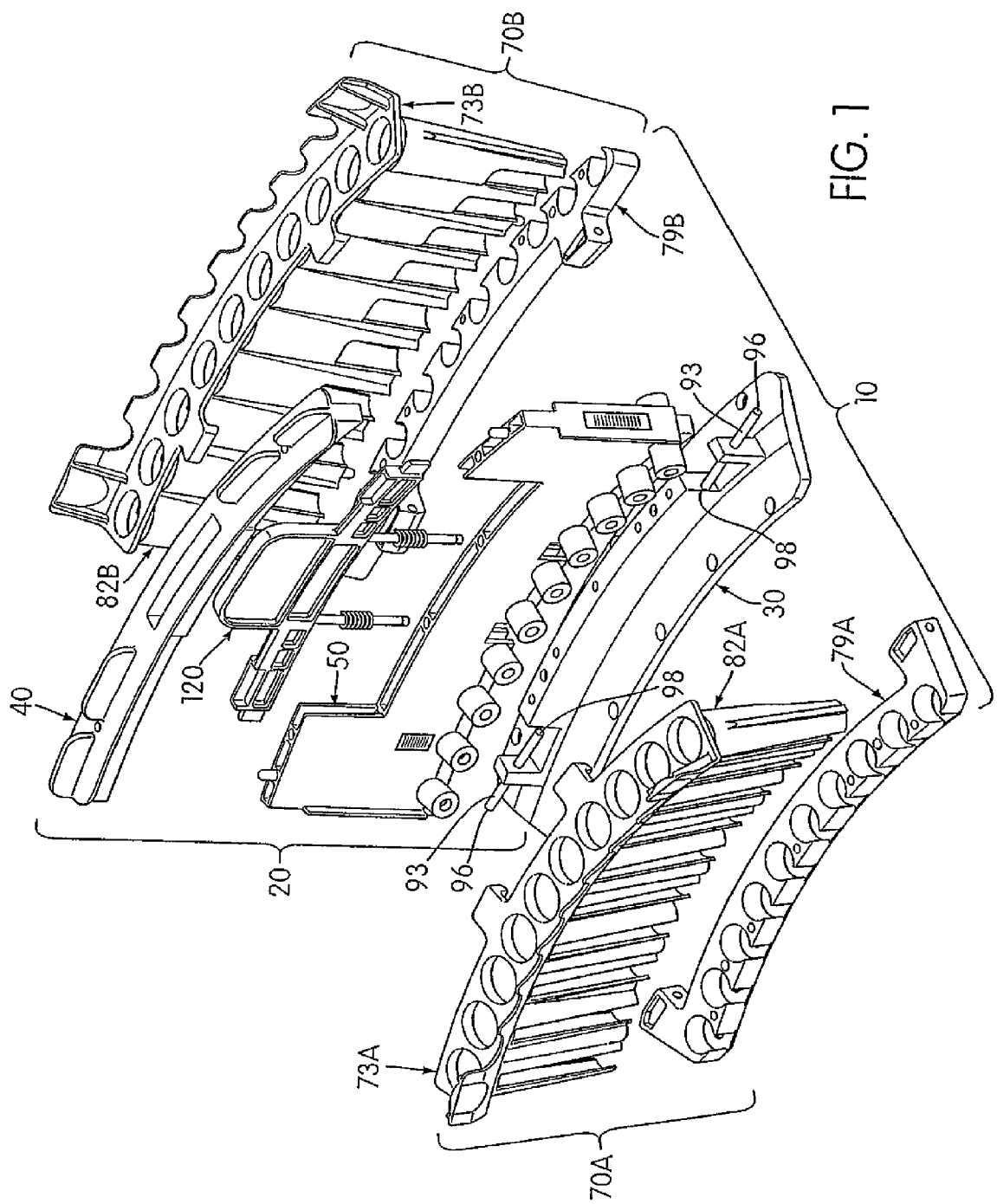
FIG. 1 is an exploded perspective view of a sample carrier according to the present invention.

The sample carrier illustrated in the attached drawings includes a number of redundant features. Where it would be clear to those skilled in the art from reviewing the drawings and reading the following description what features are being shown, the inventors have attempted to avoid including an excessive number of reference numbers by providing reference numbers for only a representative number of similar features depicted therein.

DESCRIPTION OF THE PREFERRED EMBODIMENTS

While the present invention may be embodied in a variety of forms, the following description and accompanying drawings are merely intended to disclose some of these forms as specific examples of the present invention. Accordingly, the present invention is not intended to be limited to the forms or embodiments so described and illustrated. Instead, the full scope of the present invention is set forth in the appended claims.

With reference to the figures, a preferred sample carrier 10 of the present invention is shown alone or in combination with a drip shield 200 for protecting against cross-contamination between sample tubes 300 carried by the sample carrier and for limiting vertical movement of the carrier when test sample is being removed from any of the sample tubes. Sample carriers 10 of the present invention are preferably used in combination with sample tubes 300 having sealed caps 310 which can be penetrated by conventional plastic pipette tips. (The seal is indicated in the figures with reference number 350.) To ensure proper alignment for penetrating the sealed caps 310 and pipetting test sample from a vessel component 320, the sample carriers 10 of the present invention substantially immobilize the sample tubes 300 they carry, thereby limiting both vertical and lateral movement of the sample tubes during sampling procedures. The sample tubes 300 used with the sample carriers 10 of the present invention may be transport tubes associated with sample collection kits used to receive, store and begin processing test samples for subsequent analysis, including analysis with nucleic acid-based assays or immunoassays diagnostic for a particular pathogenic organism or virus. Such test samples can include, for example, blood, urine, saliva, sputum, mucous or other bodily secretion, pus, amniotic fluid, cerebrospinal fluid, seminal fluid, tissue specimens, stool, environmental samples, food products, chemicals, powders, particles and granules. The sample tubes 300 may be of any shape or composition, provided the vessel component 320 of the sample tubes is shaped to receive and retain the material of interest (e.g., animal, environmental, industrial, food or water samples). Preferred sample 300 tubes are disclosed by Anderson et al. in U.S. Patent Application Publication No. US 2001-0041336A1 and by Kacian et al. in U.S. Patent Application Publication No. US 2002-0127147 A1.

Figure 2:
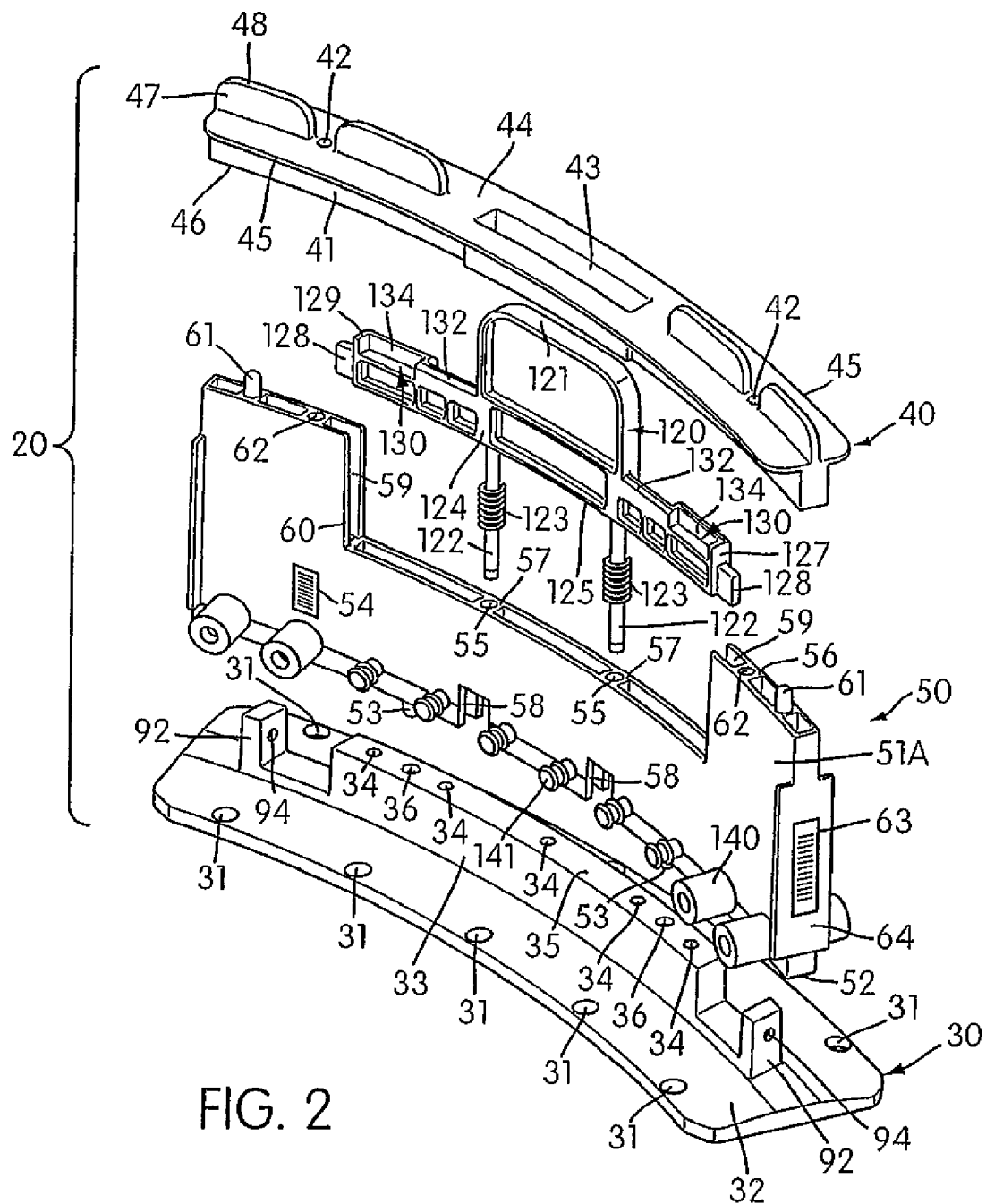
FIG. 2 is an exploded perspective view of the frame of the sample carrier of FIG. 1.
Figure 3:
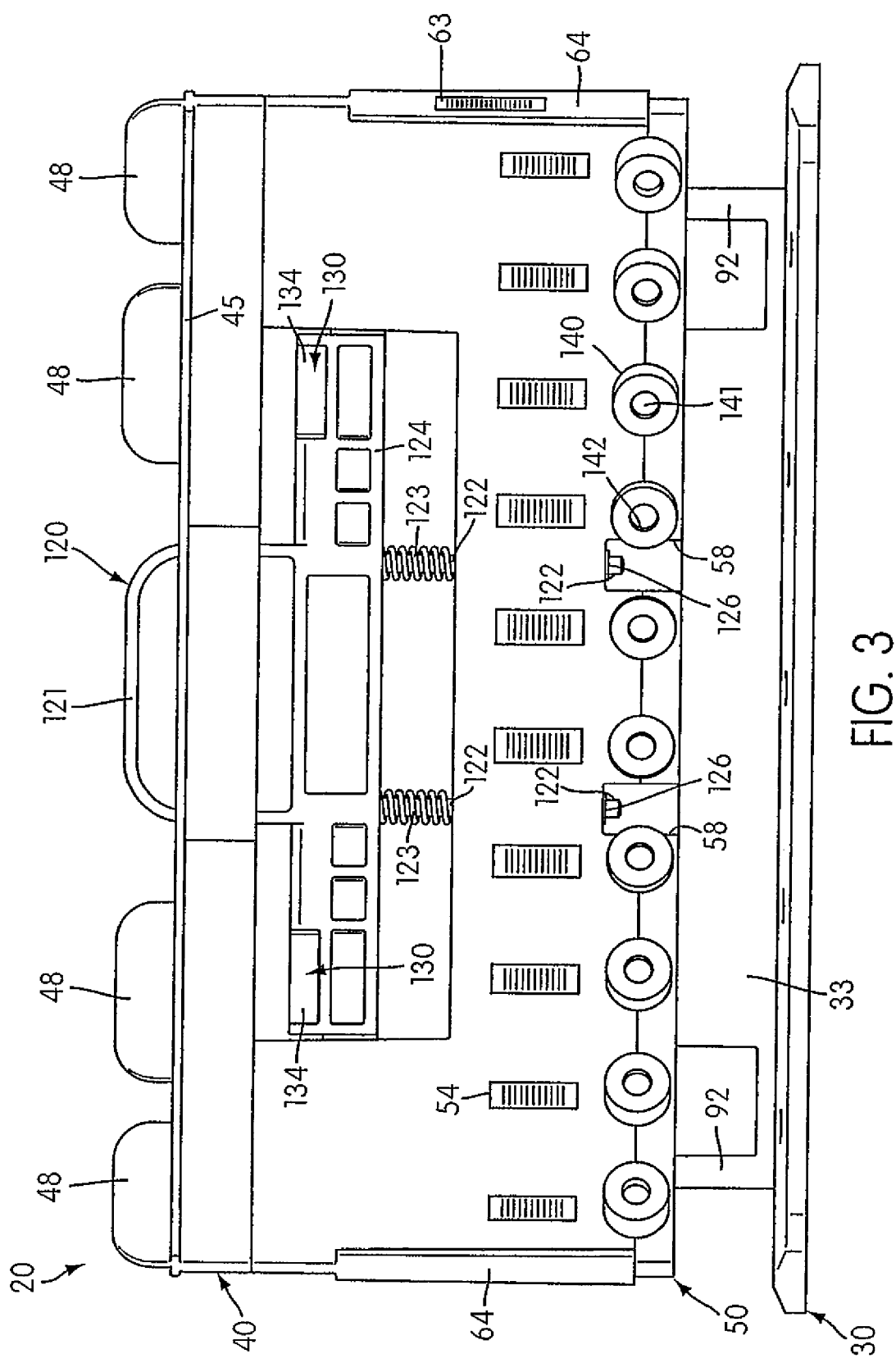
FIG. 3 is a front view of the assembled frame of FIG. 2.
Figure 17:
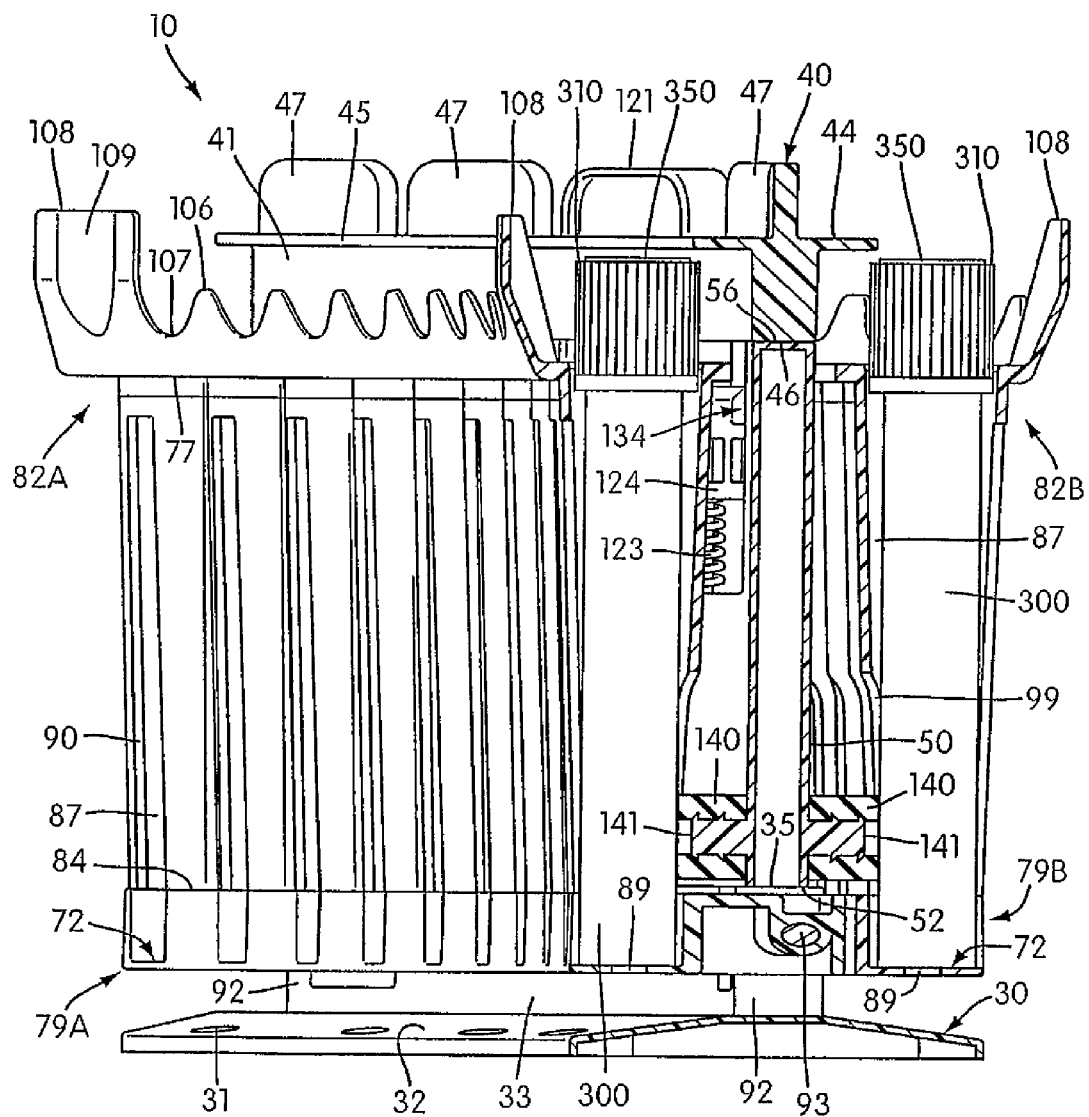
FIG. 17 is a section end view of the sample carrier of FIG. 16, taken along the 17-17 line thereof, and two sample tubes inserted into the sample tube receiving areas.

As illustrated in the figures, a sample carrier 10 according to the present invention includes a frame 20 and one or a pair of sample tube receiving structures 70A, 70B, each sample tube receiving structure having a series of apertures 71 and corresponding sample tube receiving areas 72 dimensioned to receive sample tubes 300. The frame 20 and the sample tube receiving structures 70A, 70B include means for pivoting the sample tube receiving structures relative to the frame. Hinges are provided in a preferred embodiment for joining the frame 20 and sample tube receiving structures 70A, 70B and for allowing the sample tube receiving structures to be pivoted relative to the frame. As shown in FIGS. 1-3, the frame 20 includes a base 30, a top wall 40 and a support wall 50 which joins the top wall and the base in fixed relationship to each other. The support wall 50 and the sample tube receiving structures 70A, 70B include means for releasably locking the sample tube receiving structures in substantially parallel orientations relative to the support wall. Such means could include clips, clasps or other types of fasteners. In a preferred embodiment illustrated in FIGS. 1-3, a latch 120 substantially interposed between the top wall 40 and the support wall 50 and a pair corresponding clasps 100A, 100B extending inward from a surface of each sample tube receiving structure 70A, 70B toward the support wall are provided for releasably locking the sample tube receiving structures in substantially parallel orientations relative to the support wall (see FIGS. 12 and 17). As shown, one or more springs 140 are provided on each of the side walls 51A, 51B of the support wall 50 which correspond to each sample tube receiving area 72 for immobilizing sample tubes 300 in the sample tube receiving areas when the sample tube receiving structures 70A, 70B are locked relative to the support wall. The sample carrier 10 is preferably arcuately shaped for use on a sample carousel, such as the sample carousel disclosed by Ammann et al in U.S. Pat. No. 6,335,166.

Figure 5A:
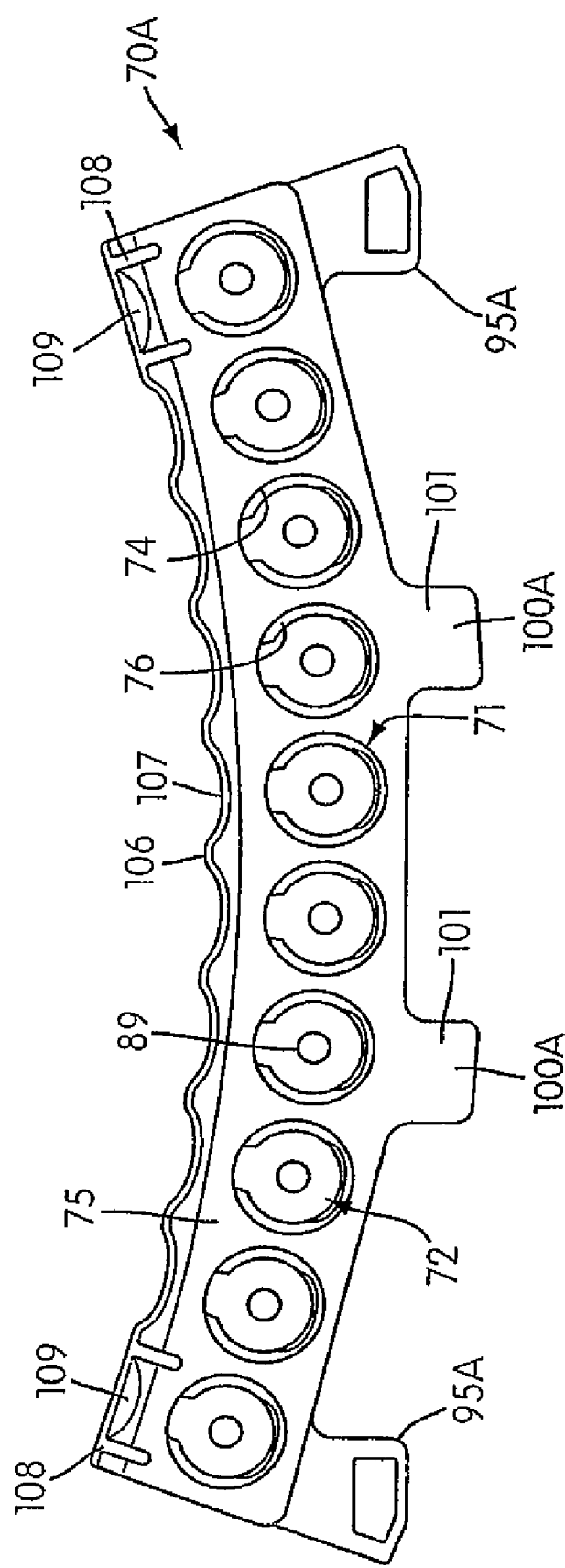
FIGS. 5A and 5B are top views of the sample tube receiving structures of FIGS. 4A and 4B, respectively.
Figure 5B:
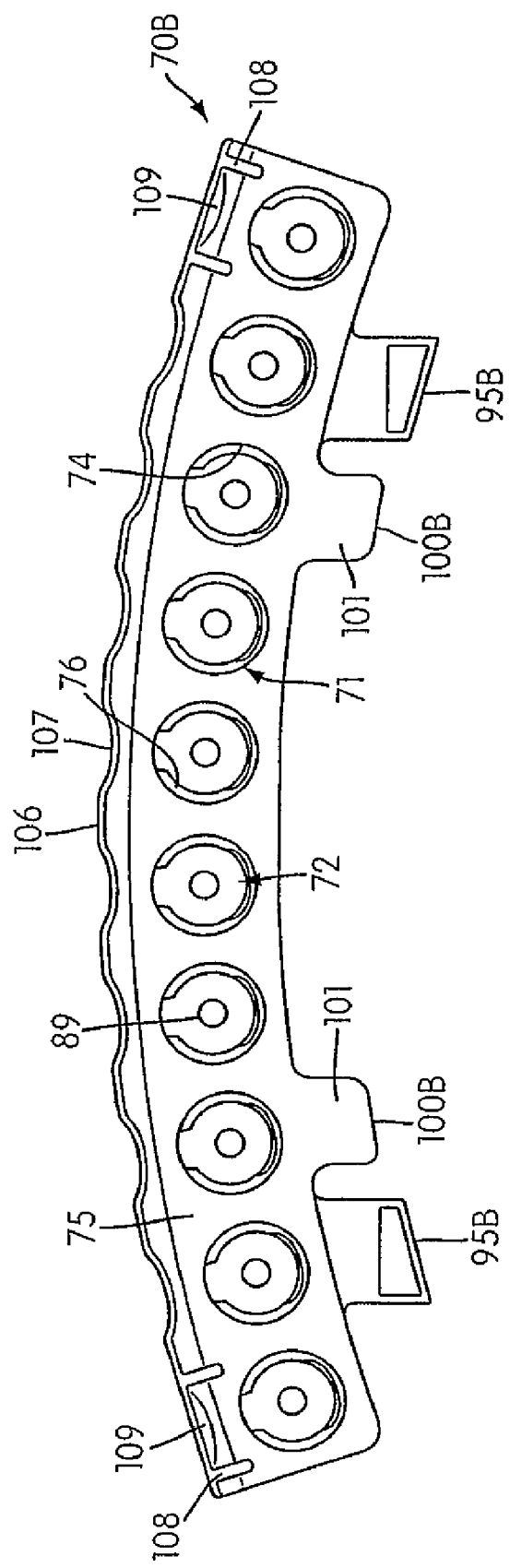

While the sample carrier 10 may include a single sample tube receiving structure (70A or 70B), a pair of sample tube receiving structures 70A, 70B joined to the frame 20 and separated by the support wall 50 is preferred, as illustrated in the figures. Each sample tube receiving structure 70A, 70B includes a series of aligned apertures 71, as discussed above, where the apertures may have the same or different dimensions. As depicted in FIGS. 5A and 5B, the apertures 71 preferably have the same dimensions, including a generally circular geometry to accommodate cylindrical sample tubes 300. The apertures 71 are formed in a top member 73 of the sample tube receiving structures 70A, 70B, and a lip 74 surrounding each aperture on a top surface 75 of the top member is preferably chamfered to facilitate insertion of sample tubes 300 into the sample tube receiving areas 72.

FIGS. 1 and 4A-5B show that the apertures 71 are circumscribed by sleeves 76 depending from a bottom surface 77 of the top member 73 and extending to a top surface 84 of each bottom member 79A, 79B. A pair of positioning bosses 80 depend from a bottom end 81 of a main structure 82A, 82B and into a corresponding pair of slots 83 in the top surface 84 of the bottom member 79A, 79B of each sample tube receiving structure 70A, 70B, where the slots are dimensioned to receive the positioning bosses and serve to facilitate attachment of the main structure to the bottom member. Each bottom member 79A, 79B also includes a plurality of through-holes 85 (see FIGS. 7A and 7B) which are aligned with threaded slots 86 in the bottom end 81 of the corresponding main structure 82A, 82B (see FIG. 6A), so that when the positioning bosses 80 are fitted into their corresponding slots 83, screws mated with the threaded slots secure the bottom member to the main structure of the sample tube receiving structure 70A, 70B. Alternatively, the sample tube receiving structures 70A, 70B may be injection molded as a unitary piece or joined together by other means, such as an adhesive, snap-fit or clasps.

Figure 9:
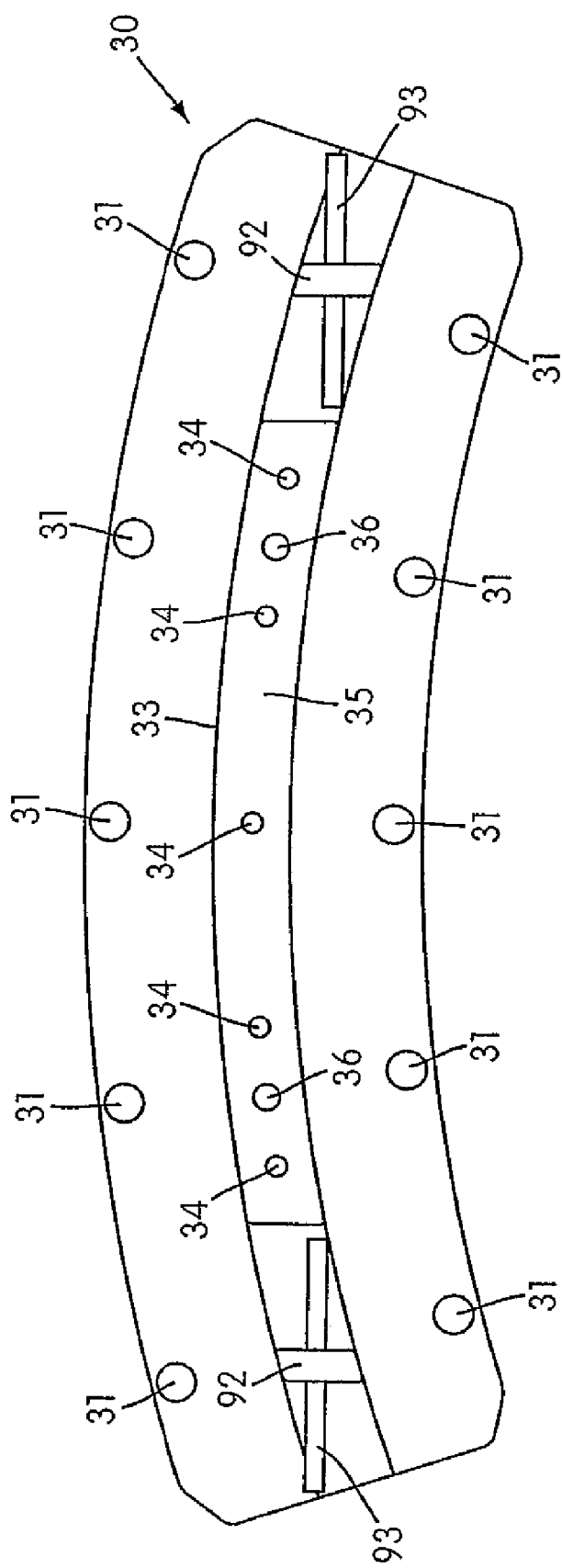
FIG. 9 is a top view of the base of the frame of FIG. 2.

Referring to FIG. 9, the base 30 of the frame 20 is provided with a plurality of through-holes 31 which are vertically aligned with the through-holes 85 in the bottom member 79A, 79B of each sample tube receiving structure 70A, 70B. The through-holes 31 are sized to provide access for screws joining the bottom members 79A, 79B to the corresponding main structures 82A, 82B of the sample tube receiving structures 70A, 70B. This access allows practitioners to separate the main structures 82A, 82B from the bottom members 79A, 79B so that the springs 140 can be replaced or removed without having to completely separate the sample tube receiving structures 70A, 70B from the frame 20.

Figure 6B:
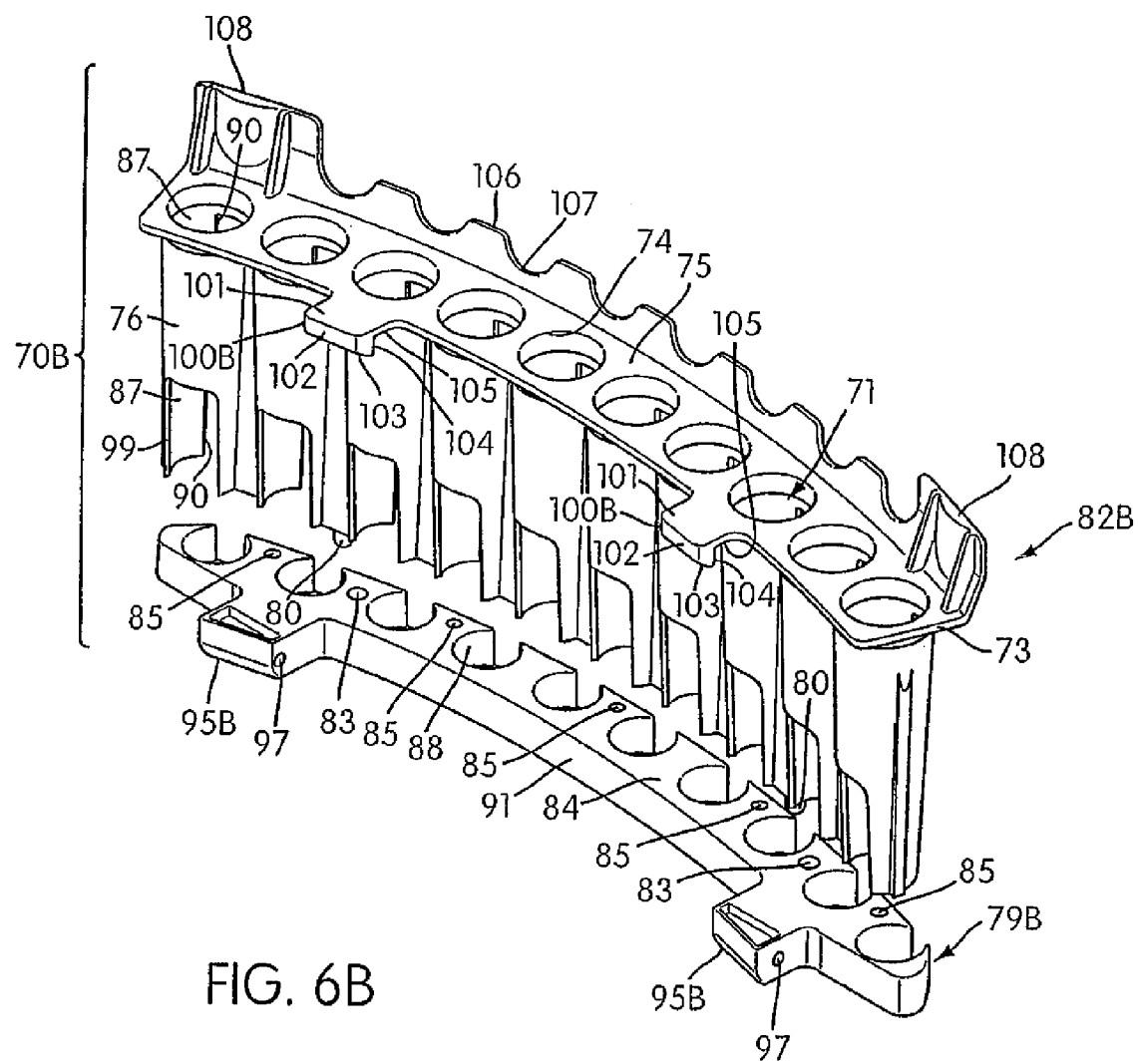

The boundaries of each sample tube receiving area 72 are determined by an inner surface 87 of each sleeve 76 and the top surface 84 of the bottom member 79A, 79B, where each sample tube receiving area is dimensioned to receive a sample tube 300 of a predetermined size. In a preferred embodiment, the top surface 84 of each bottom member 79A, 79B includes a plurality of closed or partially open bores 88 formed therein, each bore being centered beneath a sleeve 76 and dimensioned to receive the distal end of a sample tube 300, as illustrated in FIGS. 6B, 7A and 7B. The inner surfaces 87 of the sleeves 76 and corresponding apertures 71 are preferably sized to receive penetrable cap components 310 of the sample tubes 300 in touching contact or in a frictional fit, thereby allowing the longitudinal axes of the cap components 310 to move laterally from the longitudinal axes of the apertures 71 no more than about 0.125 inches (3.12 mm), and preferably no more than about 0.1 inches (2.54 mm). The sleeves 76 shown taper inward as they depend from the bottom surface 77 of the top member 73. A hole 89 is centered in the bottom member 79A, 79B of each sample tube receiving area 72 for draining corrosive agents, such as bleach, from the sample carrier 10.

To permit viewing or scanning of a human or machine readable label 330 (e.g., scannable bar code) which may be affixed to an outer surface 301 of the sample tube 300, each sleeve 76 includes an outwardly facing slot 90 formed therein, as illustrated in FIG. 8. The slots 90 shown in FIG. 8 are sized for viewing bar codes 330 affixed to sample tubes 300 positioned in the sample tube receiving areas 72.

Figure 11:
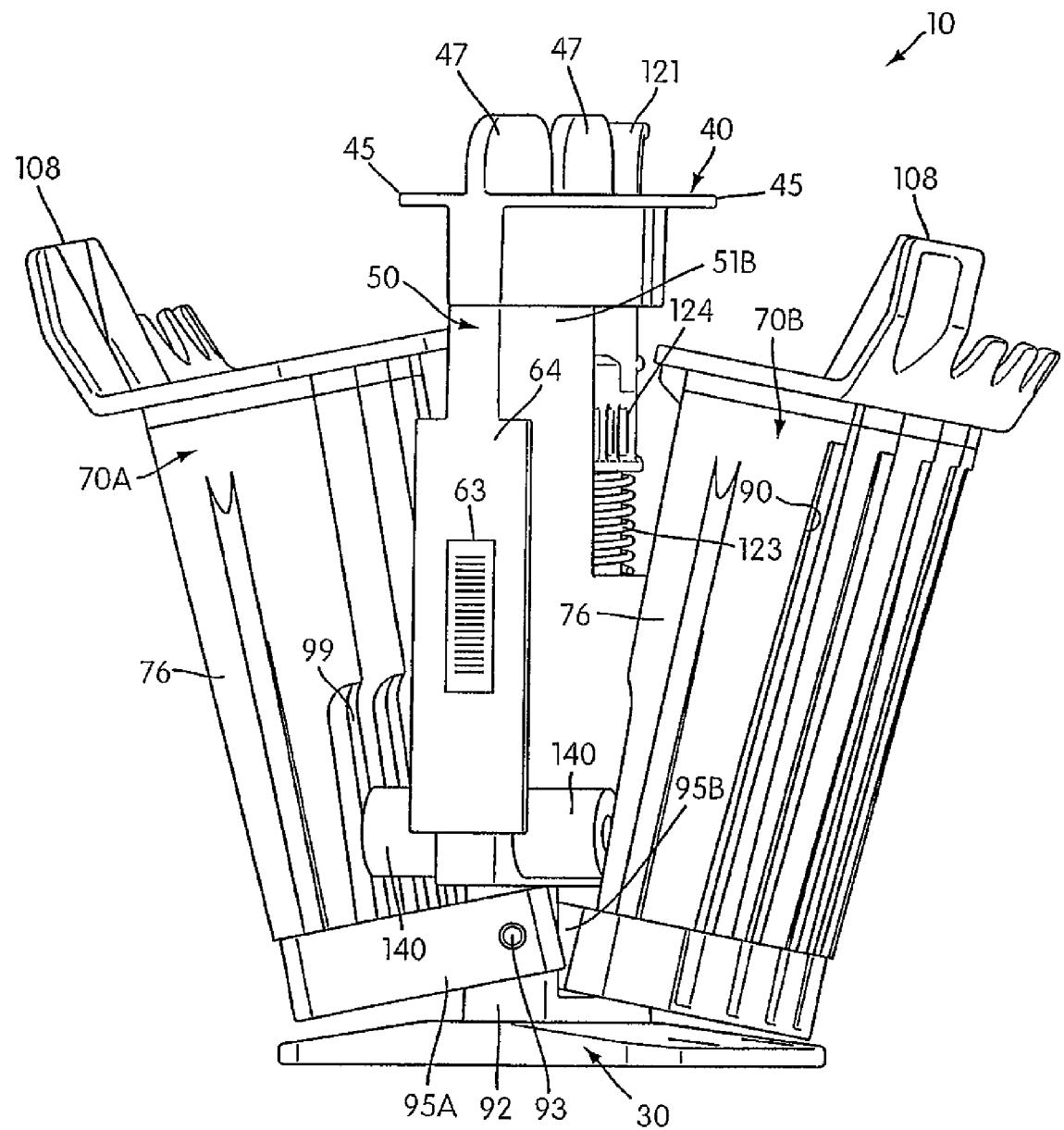
FIG. 11 is an end view of the assembled sample carrier of FIG. 1 in an "open" configuration.
Figure 12:
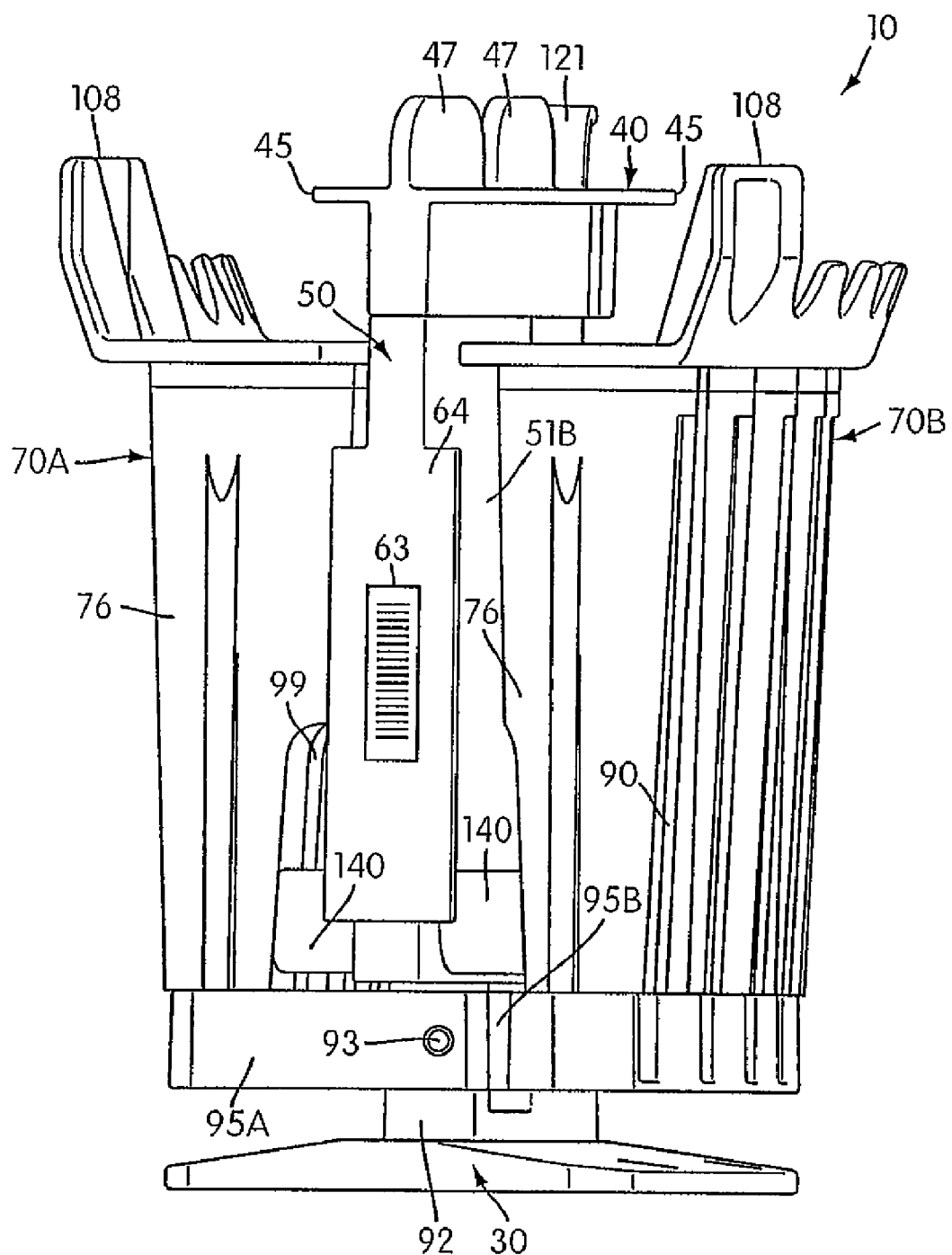
FIG. 12 is an end view of the assembled sample carrier of FIG. 1 in a "closed" configuration.
Figure 13:
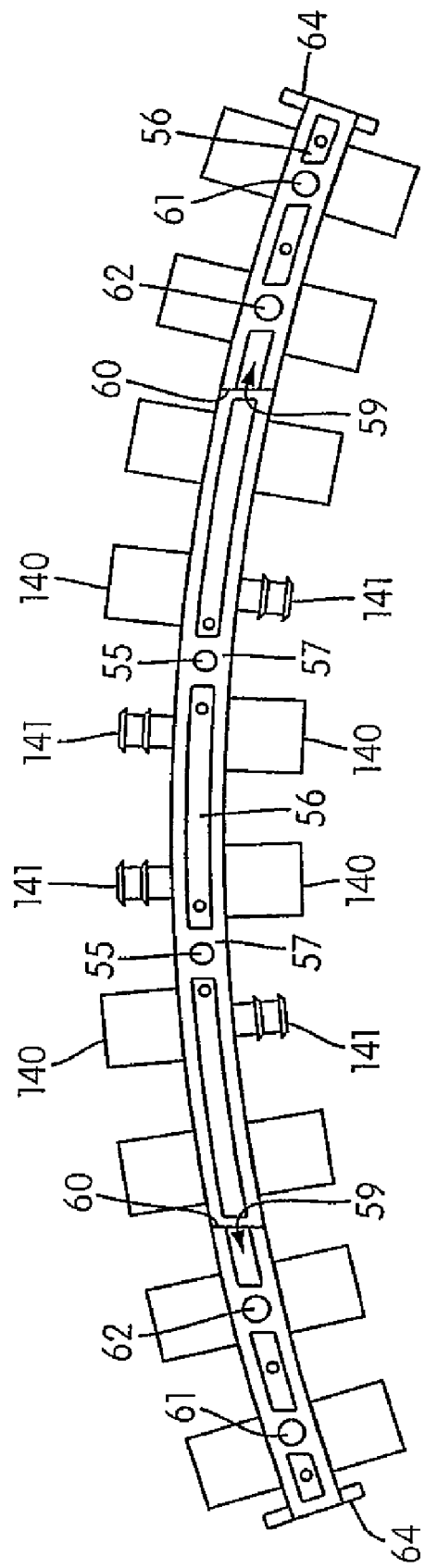
FIG. 13 is a top view of the support wall of FIG. 2.

FIGS. 1, 2 and 9 depict a pair of hinge points 92 extending upward from a top surface 32 of the base 30 which are separated by an upwardly extending mounting wall 33. A pin 93, preferably a steel pin, extends generally transversely through a through-hole 94 in each hinge point 92, and each hinge point serves to anchor a corresponding hinge clasp 95A, 95B extending from an inner surface 91 of the bottom member 79A, 79B of each sample tube receiving structure 70A, 70B. (The pins 93 extend laterally in both directions from their corresponding hinge points 92 along an imaginary line connecting the two through-holes 94 through which the pins extend. Thus, the pins 93 are not truly perpendicular to the hinge points 92 in the preferred sample carrier 10 embodiment, since the hinge points of the preferred embodiment are formed in the arcuate shape of the bottom member 79A, 79B.) An outer end 96 of each pin 93 extends into a corresponding and generally transversely oriented through-hole 97A of one of the hinge clasps 95A of one of the sample tube receiving structures 70A, and an inner end 98 of each pin extends into a corresponding and generally transversely oriented through-hole 97B of one of the hinge clasps 95B of the other sample tube receiving structure 70B (see FIGS. 6A and 6B). Once mounted on the pins 93, the sample tube receiving structures 70A, 70B are free to pivot relative to the frame 20, as illustrated in FIGS. 11 and 12.

Referring to FIG. 2, the mounting wall 33 of the base 30 is attached to a bottom wall 52 of the support wall 50. The base 30 may be joined to the support wall 50 by means of an adhesive, clamps, screws or the like. If screws are used to join the base 30 to the support wall 50, then a plurality of through-holes 34 sized to receive the screws are included in a top wall 35 of the mounting wall 33, as shown in FIG. 9. The bottom wall 52 of the support wall 50 is provided with corresponding threaded slots (not shown) for attachment of the screws. Additionally, the bottom wall 52 of the support wall 50 includes depending positioning bosses 53, as shown in FIG. 2, which are sized to fit into corresponding slots 36 in the top wall 35 of the mounting wall 33 for positioning the support wall on the base 30 (see FIGS. 3 and 9). The mounting wall 33 serves to maintain the support wall 50 above the pins 93 of the hinge points 92, so that the sample tube receiving structures 70A, 70B are free to pivot relative to the frame 20 without interference from the support wall.

Figure 4A:
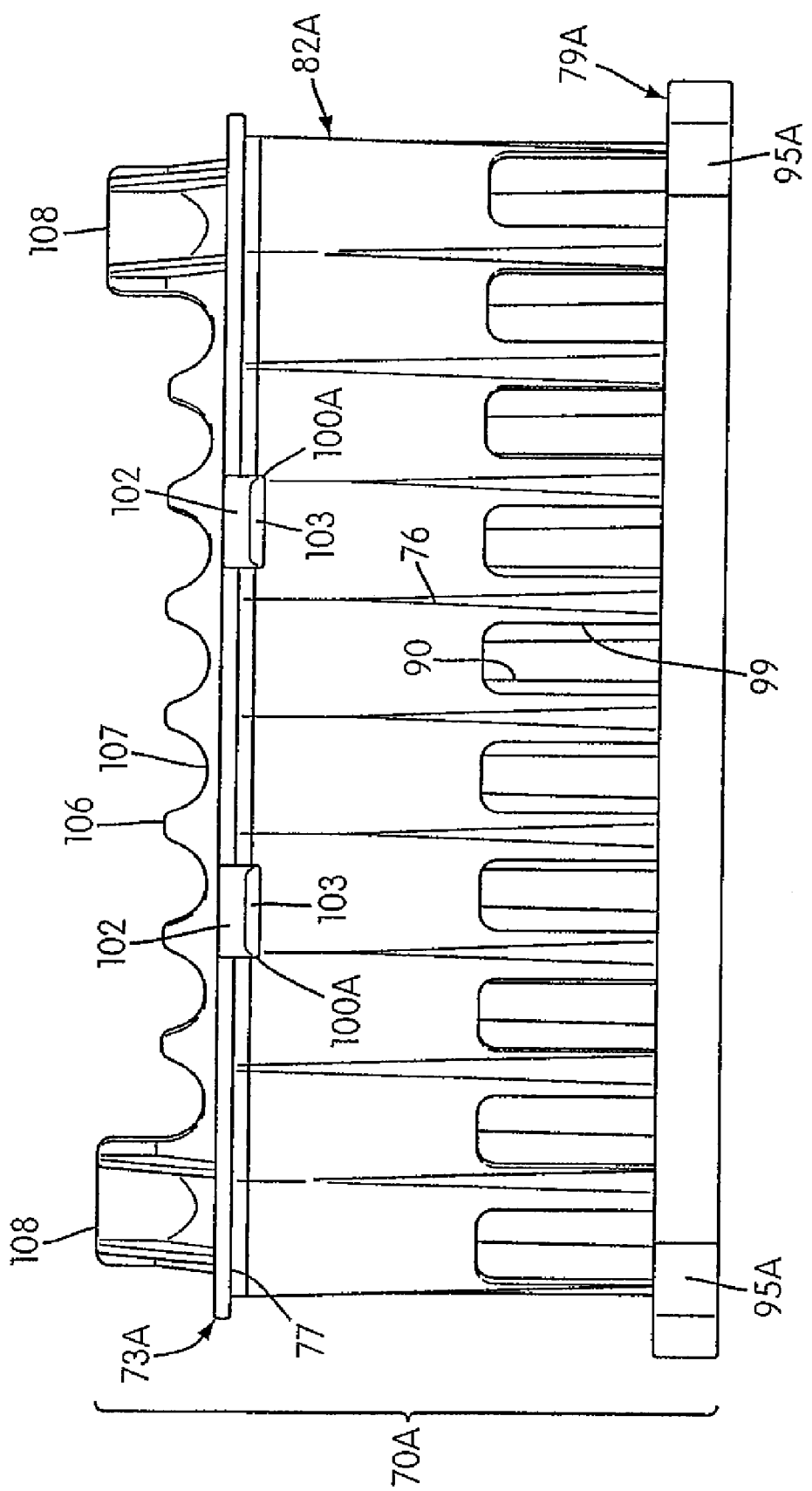
FIGS. 4A and 4B are rear views of the sample tube receiving structures of the sample carrier of FIG. 1.
Figure 4B:
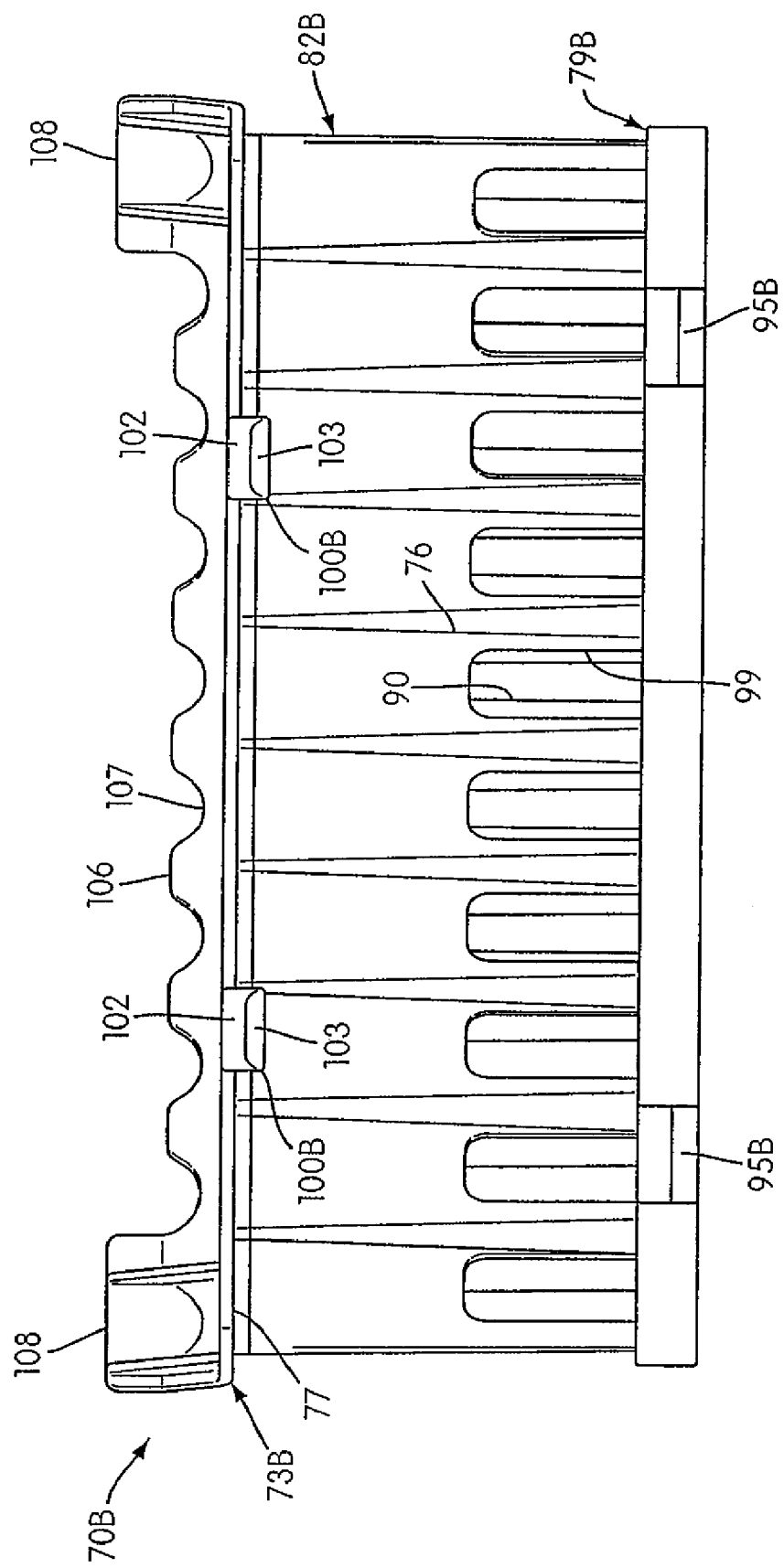

In a preferred embodiment shown in FIGS. 1-3 and 13, a plurality of springs 140 are provided on side walls 51A, 51B of the support wall 50, where each spring 140 is juxtaposed with an inwardly facing opening 99 in an opposing sleeve 76 which is sized to receive the associated spring therethrough (see FIGS. 4A and 4B). When the sample tube receiving structures 70A, 70B are in the "open" configuration shown in FIG. 11, the springs 140 do not make contact with sample tubes 300 inserted into the sample tube receiving areas 72. However, when the sample tube receiving structures 70A, 70B are in the "closed" or "locked" configuration shown in FIG. 12, the springs 140 apply a retaining force against sample tubes 300 present in the associated sample tube receiving areas 72, biasing the sample tubes against opposing inner surfaces 87 of the sleeves 76. The sample tube retaining force of each spring of the present invention is preferably at least about 3 pounds force (13.34 N). Preferred springs of the present invention are constructed of a rubber which resists acids and bleaches associated with many assay protocols, such as Viton®, a fluorelastomer available from DuPont Dow Elastomers L.L.C. of Wilmington, Del.

The springs 140 may be secured to the support wall 50 by any suitable attachment means, such as, for example, pins 141 extending generally transversely through the support wall which are inserted through centrally located bores 142 in the springs, as shown in FIG. 3. In this embodiment, the pins 141 can hold the springs 140 in a frictional or interference fit. Preferred pins are made of steel and have barbed ends, as shown in FIG. 2, which are positioned in the support wall 50 during an injection molding procedure and which provide for an interference fit. A frictional fit could be achieved with rod-like pins and would advantageously allow the springs 140 to be readily replaced or exchanged without causing damage to the pins. Other attachment means could include, for example, screws extending through centrally located bores in the springs 140 which are secured to corresponding slots (not shown) in the support wall 50 having matched threads for receiving the screws.

In an alternative embodiment, a single spring (not shown) may be associated with two or more sample tube receiving areas 72. For this embodiment, the material of the spring, such as a rubber, would need to be constructed and arranged on the side walls 51A, 51B of the support wall 50 so that the spring or springs do not physically contact any of the sleeves 76 when the sample tube receiving structures 70A, 70B are in the closed configuration depicted in FIG. 12. Otherwise, the spring or springs might be hindered from exerting a sufficient retaining force against the sample tubes 300 to maintain the sample tubes in their corresponding sample tube receiving areas 72 during use.

If a leaf spring is affixed to the support wall 50, it may be desirable to treat a surface of the spring which will come into contact with a sample tube 300 to increase the coefficient of friction between the spring and an outer surface of the sample tube. The surface of the spring may be chemically or physically altered, such as by sand-blasting or etching a surface of the spring using techniques well known in the art.

Referring to FIG. 8, the slots 90 and openings 99 formed in opposed portions of each sleeve 76 may be configured and arranged so that properly sized machine readable labels 54 (e.g., scannable bar codes) affixed to areas of the side walls 51A, 51B of the support wall 50 immediately above the springs 140 would be visible when the sample carrier 10 is in the closed configuration shown in FIG. 12. If the test samples were substantially opaque (e.g., blood) and consumed a sufficient volume of the sample tubes 300 to block the machine readable labels 54, the machine readable labels could be useful for providing information about the presence or absence of a sample tube 300 in a particular sample tube receiving area 72. This information would be based solely on whether the machine readable label 54 is visible to a label reader on an associated automated sampling device. However, the machine readable labels 54 would not be useful for providing "tube present" information if the test samples in the sample tubes 300 are substantially transparent, such as urine or plasma samples, or the material of the sample tubes is opaque. In the former case, the test samples could actually magnify the machine readable label.

FIGS. 1-3 illustrate the positioning of the latch 120 between the support wall 50 and the top wall 40. The latch includes a handle 121, a pair of guide rods 122, a coil spring 123 disposed on each guide rod, and a transverse structure 124 interposed between and connecting the handle and the guide rods. The guide rods 122 are constructed and arranged to be fitted into a pair of slots 55 positioned on a recessed section of a top surface 56 of the support wall 50. When the guide rods 122 are fitted into the slots 55, a distal portion of each coil spring 123 is in touching contact with a rim 57 circumscribing each corresponding slot. The coil springs 123 may extend the length of the exposed guide rods 122 when the guide rods are inserted into the slots 55 or, alternatively, proximal ends of the coil springs may be immobilized on the guide rods by such means as welding or by including perpendicularly extending protuberances on the guide rods which limit vertical movement of the coil springs. In the embodiment illustrated in FIG. 3, the proximal ends of the coil springs 123 are in touching contact with a bottom surface 125 of the transverse structure 124. The slots 55 are sized to permit downward movement of the guide rods 122 when the handle 121 is depressed.

FIG. 3 shows a preferred latch 120 having C-rings 126 attached to distal ends of the guide rods 122 below the coil springs 123. The C-rings 126 are provided to the guide rods 122 to limit upward movement of the latch 120 so that the clasps 100A, 100B are properly aligned with and engage the transverse structure 124 in the manner describe infra, forcing the latch downward and generating the closed position of the sample carrier 10 shown in FIG. 12. A pair of windows 58 are formed in the side walls 51A, 51B of the support wall 50 to provide access to the guide rods 122 for fixing the C-rings 126 thereto.

Figure 14:
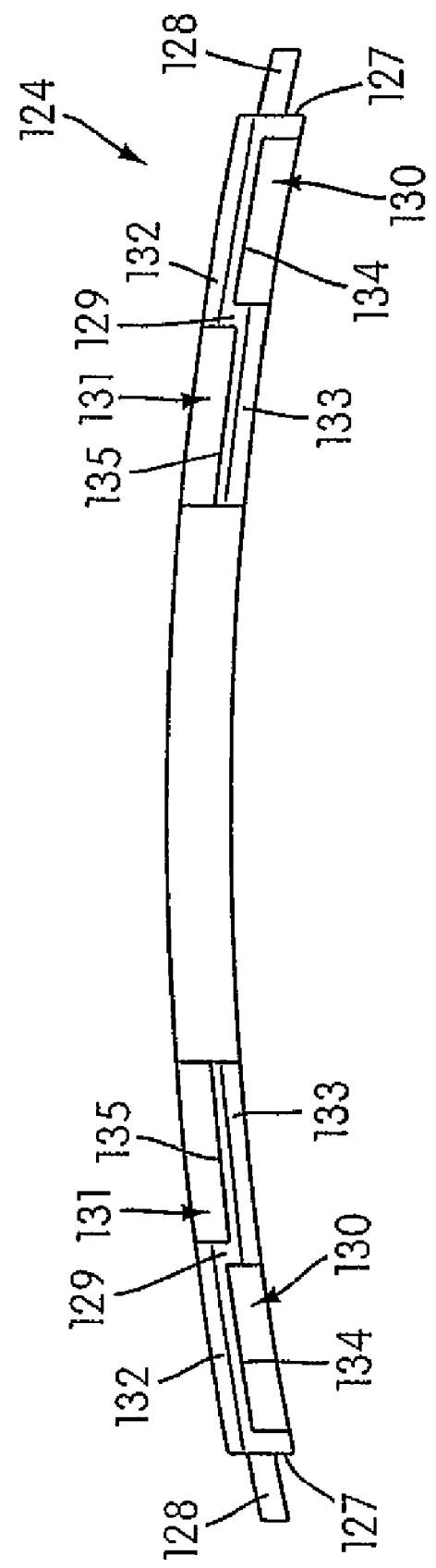
FIG. 14 is a top view of the transverse structure of FIG. 2.

As shown in FIGS. 2 and 14, lateral ends 127 of the transverse structure 124 are provided with laterally extending tabs 128 sized to fit in sliding engagement within vertical slots 59 extending along the length of opposed inner walls 60 of the support wall 50. A top surface 129 of the transverse structure 124 includes a pair of depending inner and outer recesses 130, 131 positioned on opposite sides of the handle 121, where each recess 130, 131 corresponds to one of the clasps 100A, 100B extending inward toward the latch 120 from the top member 73 of one of the sample tube receiving structures 70A, 70B, and each sample tube receiving structure includes a pair of clasps. Each clasp 100A, 100B, in turn, has a flat top surface 101, an end surface 102, and a downwardly sloped bottom surface 103 extending toward the sleeves 76 of the corresponding sample tube receiving structure 70A, 70B from the end surface, where the sloped bottom surface terminates at a vertical surface 104 depending from a flat bottom surface 105 of the clasp, as illustrated in FIGS. 6A and 6B.

Figure 10A:
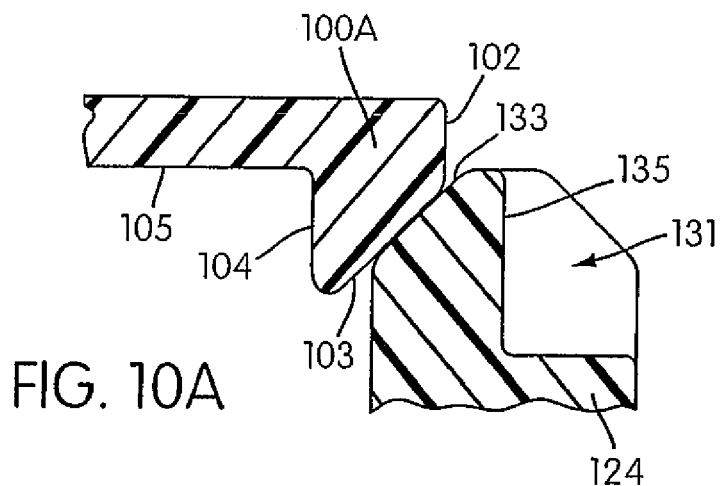
FIGS. 10A-C illustrate a series of steps for locking of the sample tube receiving structures to the frame of FIG. 1.
Figure 10B:
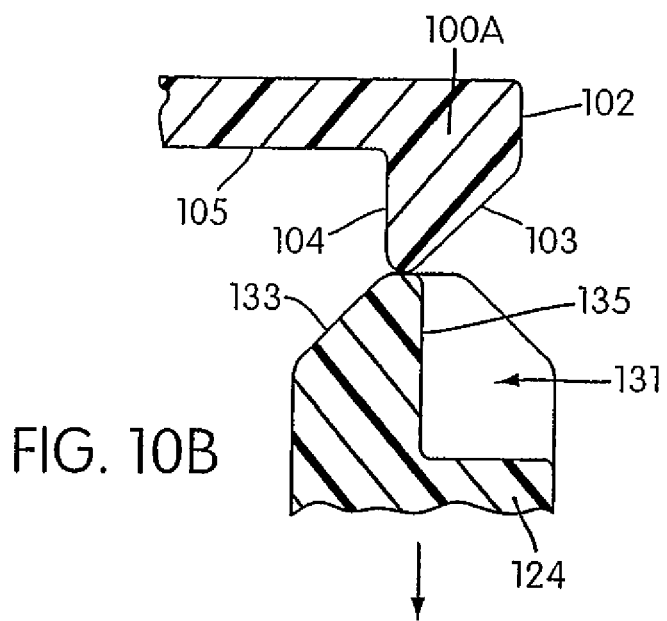

When one or both sample tube receiving structures 70A, 70B are pivoted toward the latch 120, as depicted in FIG. 10A, the sloped bottom surfaces 103 of the clasps 100A, 100B contact outer, rounded or beveled edges 132, 133 of the top surface 129 of the transverse structure 124 opposite corresponding recesses 130, 131, respectively. FIG. 10B shows that further inward pressure against one or both sample tube receiving structures 70A, 70B forces the latch 120 downward as the sloped bottom surfaces 103 of the clasps 100A, 100B slide over the outer edges 132, 133 of the top surface 129, and as the guide rods 122 are forced into the slots 55 in the support wall 50, against the resistance of the coil springs 123. The tabs 128, which are constructed and arranged on the transverse structure 124 to provide a caged sliding motion within the corresponding vertical slots 59 of the support wall 50, are also included so that the latch 120 exerts a horizontal resistance against the clasps 100A, 100B as the clasps are forced against the transverse structure.

Figure 10C:
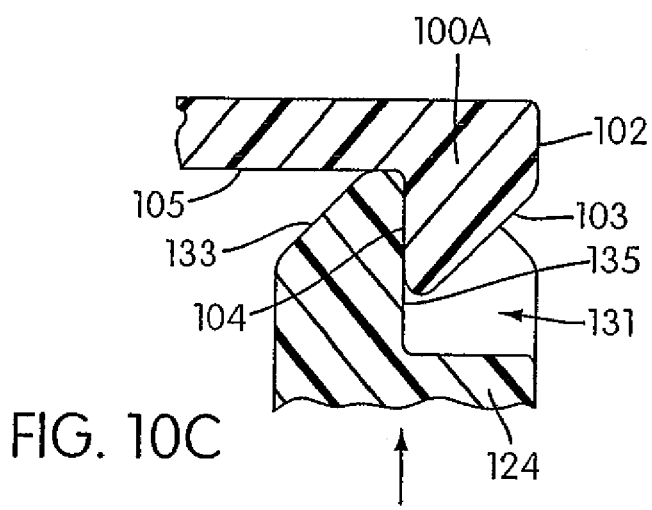

Once the sloped bottom surfaces 103 have cleared the top surface 129 of the transverse structure 124, the coil springs 123 force the transverse structure upward until the top surface of the transverse structure contacts the flat bottom surfaces 105 of the clasps. 100A, 100B, as illustrated in FIG. 10C. In this position, the vertical surfaces 104 of the clasps 100A, 100B are in inter-locking contact with opposing vertical surfaces 134, 135, respectively, on the transverse structure 124, thereby holding the sample tube receiving structures 70A, 70B in substantially parallel orientations relative to the support wall 50. The sample tube receiving structures 70A, 70B can be released from the transverse structure 124 by exerting a downward force on the handle 121 until the vertical surface 104 of each clasp 100A, 100B has cleared the top surface 129 of the transverse structure. Once the clasps 100A, 100B have been released from the transverse structure 124, the sample tube receiving structures 70A, 70B can be pivoted away from the support wall 50, thereby assuming the open configuration depicted in FIG. 11, so that one set of sample tubes 300 can be removed from the sample tube receiving areas 72 and replaced with a new set of sample tubes for sample processing.

Figure 15:
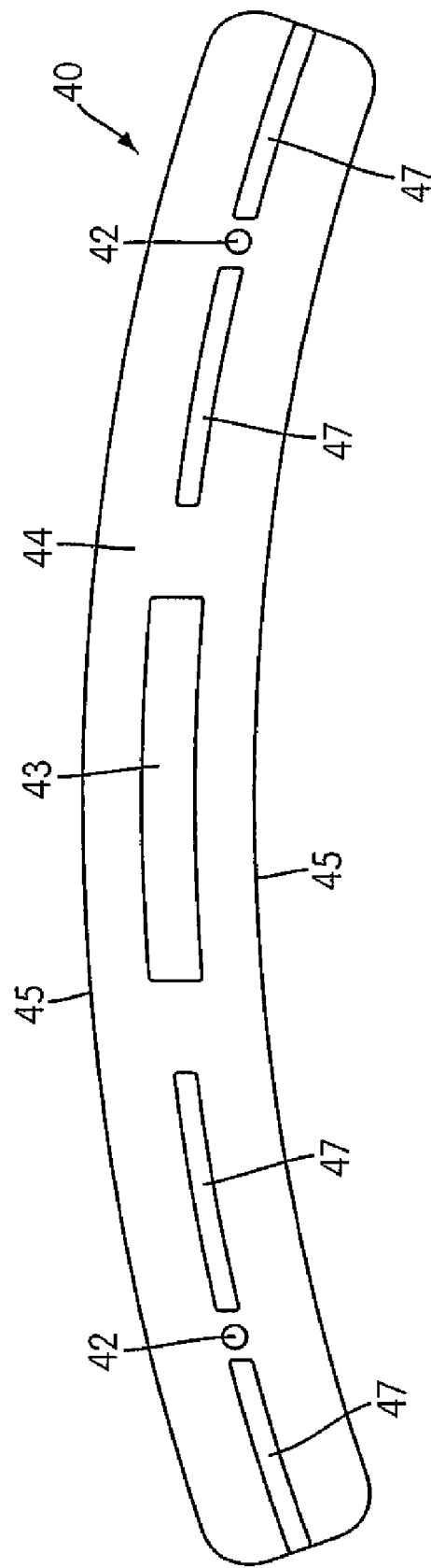
FIG. 15 is a top view of the top wall of FIG. 2.

FIG. 3 shows the top wall 40 joined to the support wall 50. The top wall 40 includes a mounting wall 41 which is joined to the top surface 56 of the support wall 50 (see FIG. 13). As illustrated in FIG. 2, the support wall 50 includes a pair of positioning bosses 61 which extend upward from the top surface 56 and are sized to fit within a pair of corresponding slots (not shown) on a bottom surface of the mounting wall 41 for positioning the top wall on the support wall. Attachment means are included for fixing the top wall 40 to the support wall 50, which preferably include a pair of through-holes 42 in the top wall (see FIG. 15) that correspond to a pair of threaded slots 62 in the support wall (see FIG. 13) for screwing the top wall to the support wall. Other attachment means could include, for example, an adhesive, clips, clasps or other fasteners.

The top wall 40 also includes a centrally positioned slot 43 which is sized to receive at least a portion of the handle 121 of the transverse structure 124 therethrough when the top wall is joined to the support wall 50. The handle 121 extends a sufficient distance above a top surface 44 of the top wall 40 to permit the clasps 100A, 100B to be released from the transverse structure 124 when the handle is depressed.

Figure 16:
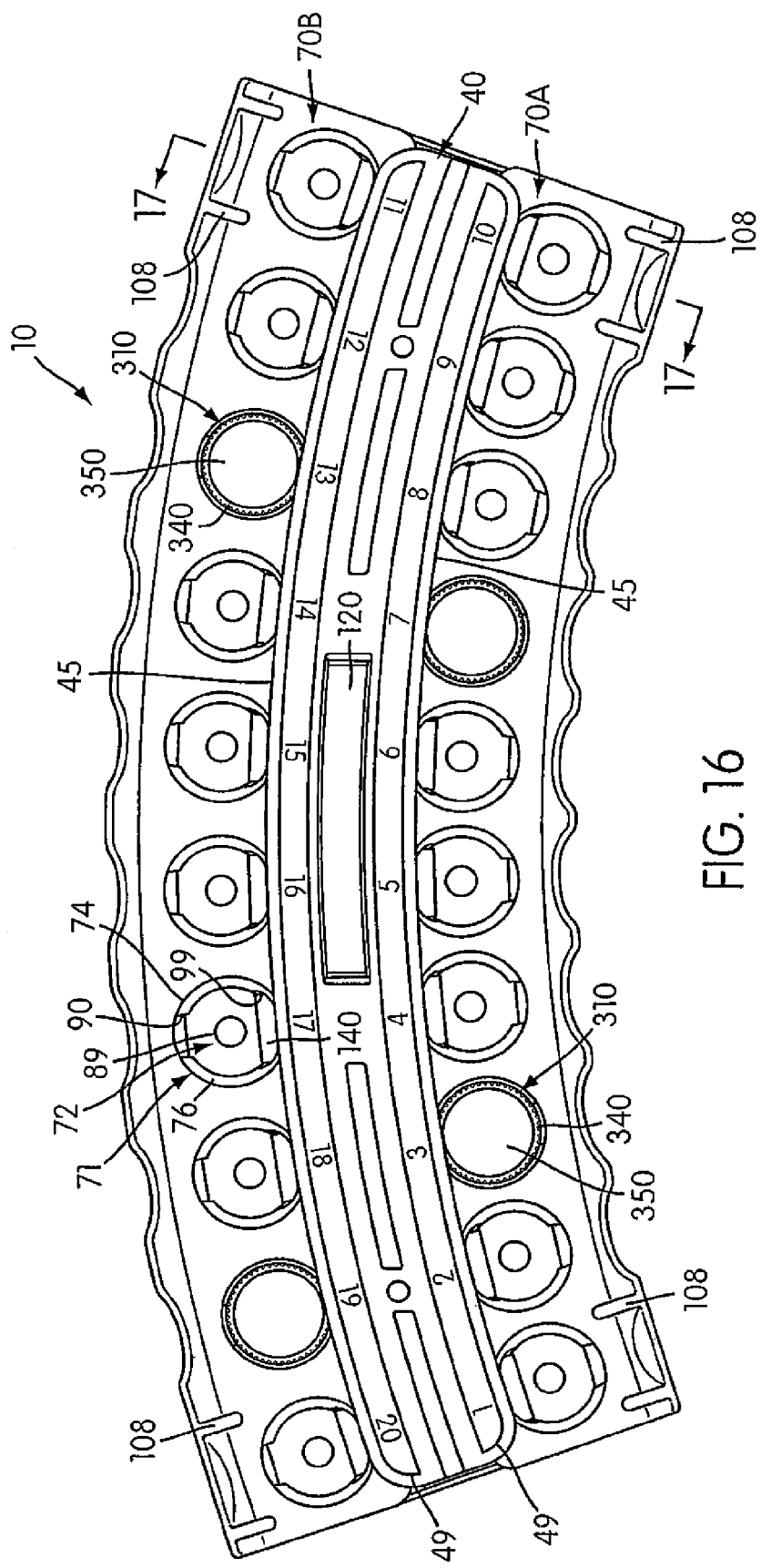
FIG. 16 is a top view of the sample carrier of FIG. 12.

Referring to FIGS. 12 and 16, edges 45 of the top wall 40 extend laterally over a portion of each sample tube receiving structure 70A, 70B when the sample carrier 10 is in the closed configuration. The edges 45 of the top wall 40 partially overhang the apertures 71 of the sample tube receiving areas 72, but do not overhang the apertures to an extent that access to sample tubes 300 in the sample tube receiving areas by a robotic pipettor is blocked or impeded. The overhangs formed by the top wall 40 function as failsafes when the sample carrier 10 is in the closed configuration by limiting vertical, upward movement of sample tubes 300 present in the sample tube receiving areas 72. This is important because removal of a sample tube 300 from a sample tube receiving area 72 could occur if the sample tube included a penetrable cap component 310 exerting a high withdrawal force against a pipette tip and/or the retaining force against the sample tube was affected by, for example, a rubber spring 140 becoming coated with a slippery fluid during sample processing. The bottom surfaces 46 of the overhangs are vertically higher than top surfaces 340 of sample tubes 300 fully inserted into the sample tube receiving areas 72, so that the sample carrier 10 can assume the closed configuration illustrated in FIG. 12.

To accommodate handling of the sample carrier 10, the top member 73 of each sample tube receiving structure 70A, 70B includes an upwardly extending outer edge 106, as shown in FIGS. 1, 4A-6B and 8. The outer edges 106 flare upward from the top member 73 in a preferred embodiment, although they may have a horizontal or vertical orientation. The illustrated outer edges 106 include a plurality of recesses 107, where each recess is positioned adjacent one of the apertures 71 to provide access to and to facilitate manual manipulation of the sample tubes 300. The outer edges 106 at the ends of the sample tube receiving structures 70A, 70B include finger extensions 108 having indentations 109 formed therein to facilitate manual engagement of the clasps 100A, 100B and latch 120 of the sample carrier 10. Engagement of the clasps 100A, 100B and latch 120 results in the closed configuration shown in FIG. 12.

Figure 18:
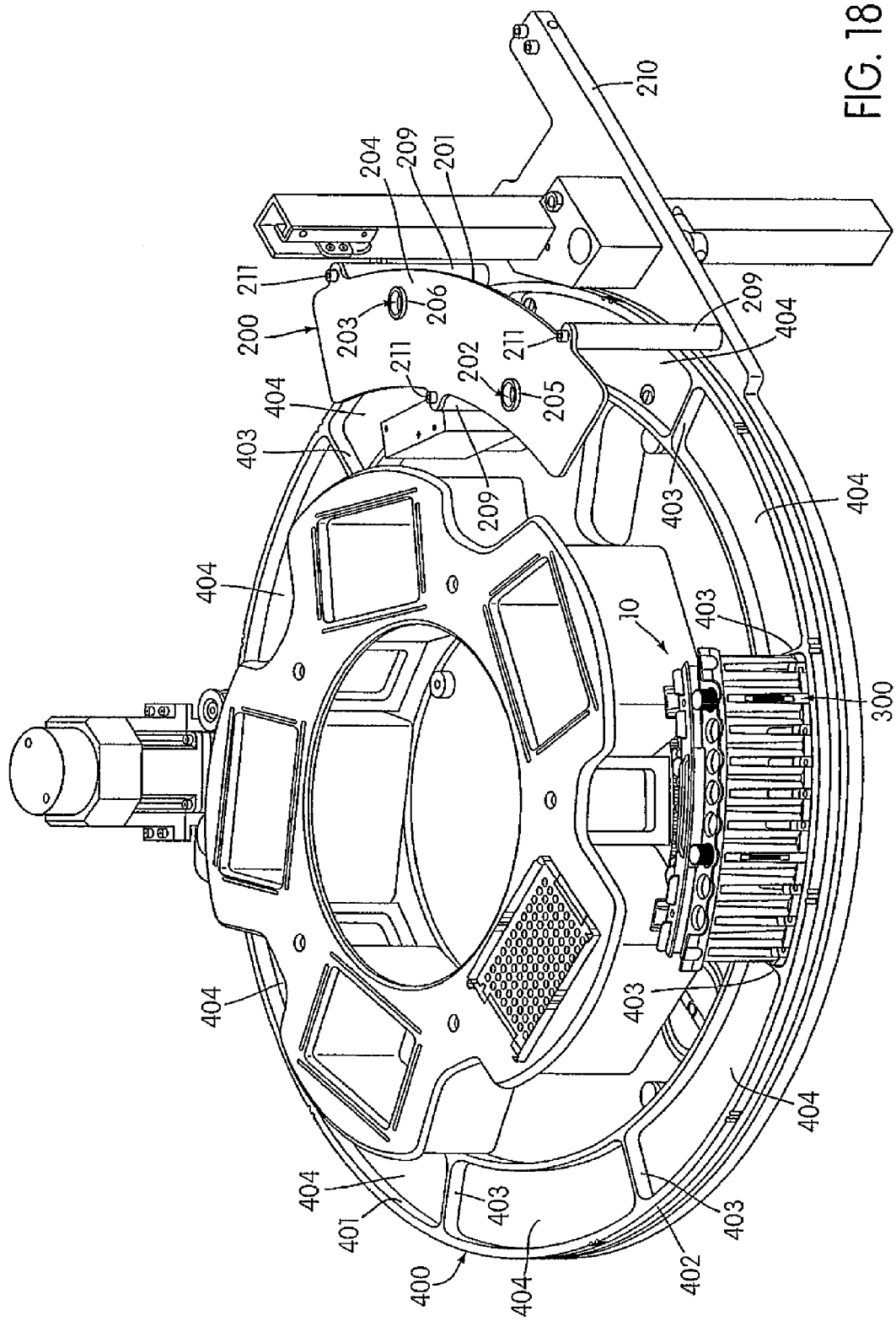
FIG. 18 shows the sample carrier of FIG. 12 positioned on a sample carousel and holding two sample tubes.

The base 30 of the sample carrier 10 may be adapted for use with a sample carrier conveying means, such as a sample carousel for rotating a plurality of sample carriers within an automated sampling system. One such sample carousel 400 is disclosed by Ammann et al. in U.S. Pat. No. 6,335,166 and is illustrated in FIG. 18. This particular sample carousel 400 is formed of milled, unhardened aluminum and includes an annular trough 401 about the periphery of a ring 402 and a plurality of raised, radially extending dividers 403. The dividers 403 divide the trough 401 into nine arcuate sample carrier receiving wells 404 which can be configured to accommodate the sample carriers 10 of the present invention. The individual sample carrier receiving wells 404 are dimensioned to maintain the sample carriers 10 in an upright position as sample tubes 300 held by the sample carriers 10 are indexed under a robotic pipettor (not shown) for retrieving sample material for analysis. To track individual sample carriers 10 on the sample carousel, the sample carriers could include an area for receiving a machine readable label 63 (e.g., scannable bar code), such as an end wall 64 of the support wall 50, as illustrated in FIGS. 11 and 12.

Figure 19:
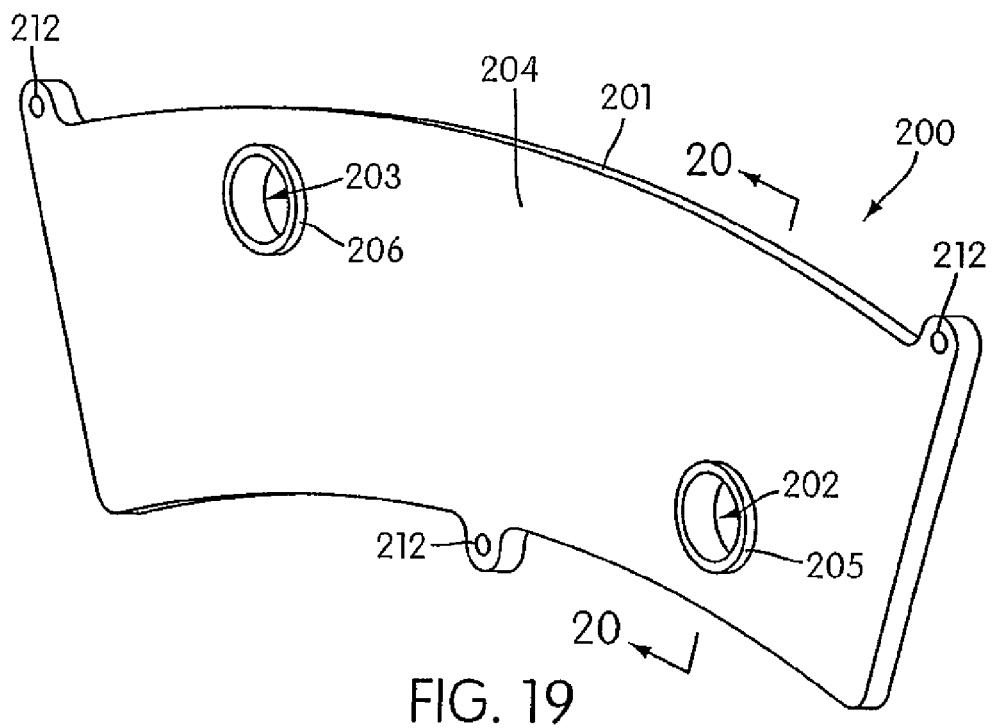
FIG. 19 is a perspective top view of a drip shield for use with an automated sampling system according to the present invention.
Figure 20:
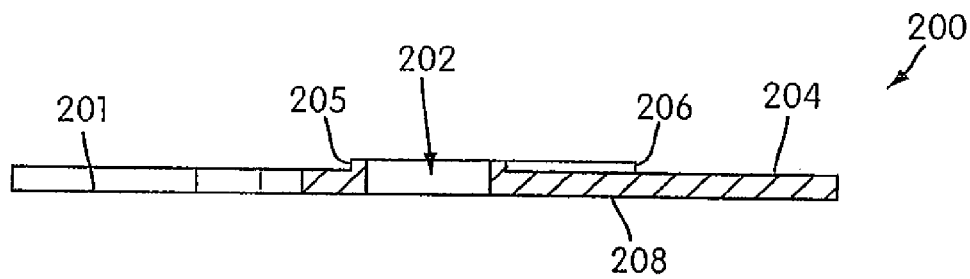
FIG. 20 is a section end view of the drip shield of FIG. 19, taken along the 20-20 line thereof.
Figure 21:
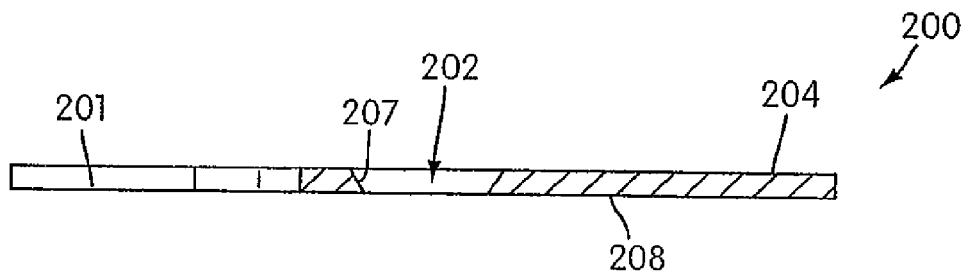
FIG. 21 is a section end view of an alternative drip shield for use with an automated sampling system according to the present invention.

The sample carriers 10 of the present invention can be used in combination with a device for protecting sample tubes 300 during sampling to further limit opportunities for cross-contamination. Such a device is provided by a drip shield 200 depicted in FIGS. 18-22. This drip shield 200 includes a cover plate 201 which is dimensioned to form a canopy over a sample carrier 10 fully contained thereunder. Thus, in a preferred embodiment, the drip shield 200 has an arcuate shape corresponding to the preferred arcuate shape of the sample carrier 10, as shown in FIG. 18. A minimum of two through-holes, identified in FIGS. 19-21 as a first through-hole 202 and a second through-hole 203, extend through the drip shield 200 and provide access to sample tubes 300 centered below the through-holes. The through-holes 202, 203 are dimensioned to permit non-interfering passage therethrough by pipette tips carried by a robotic pipettor, but are small enough so that a top surface 204 of the drip shield 200 can function to catch hanging droplets which are dislodged from the pipette tips during sample transfer procedures. Therefore, the diameters of the first and second through-holes 202, 203, respectively, are preferably about the same as or less than the smallest diameter of any cap 310 of a sample tube 300 to be carried by a sample carrier 10. Raised annular rims 205, 206 can be provided about the periphery of the first and second through-holes 202, 203, respectively, to impede fluid collected on the top surface 204 of the cover plate 201 from spilling into any of the sample tubes 300, as shown in FIGS. 19 and 20. In a preferred embodiment illustrated in FIG. 21, however, the top surface 204 of the cover plate 201 includes a chamfered ring 207 about the periphery of the first and second through-holes 202, 203, respectively, to aid in redirecting misaligned pipette tips.

The through-holes 202, 203 are arranged on the drip shield 200 so that the first through-hole 202 is positioned above a first or inner row of longitudinally or arcuately aligned sample tubes 300 and the second through-hole 203 is aligned above a second or outer row of longitudinally or arcuately aligned sample tubes. As the sample carrier 10 is indexed forward under the drip shield 200 by the sample carousel 400, the next sample tube 300 in each row of tubes can be presented under one of the through-holes 202, 203 for access by a robotic pipettor. An example of a robotic pipettor for use with the present invention is the Robotic Sample Processor, Model No. RSP9000, available from Cavro, Inc. of Sunnyvale, Calif. The through-holes 202, 203 are preferably offset on the drip shield 200 to further minimize opportunities for contamination resulting from released hanging droplets of sample. In a preferred mode, the through-holes 202, 203 are arranged on the drip shield 200, as shown in FIG. 18, so that the first sample tube 300 in the second or outer row of aligned tubes is being sampled as the third sample tube in the first or inner row of aligned tubes is being sampled.

Figure 22:
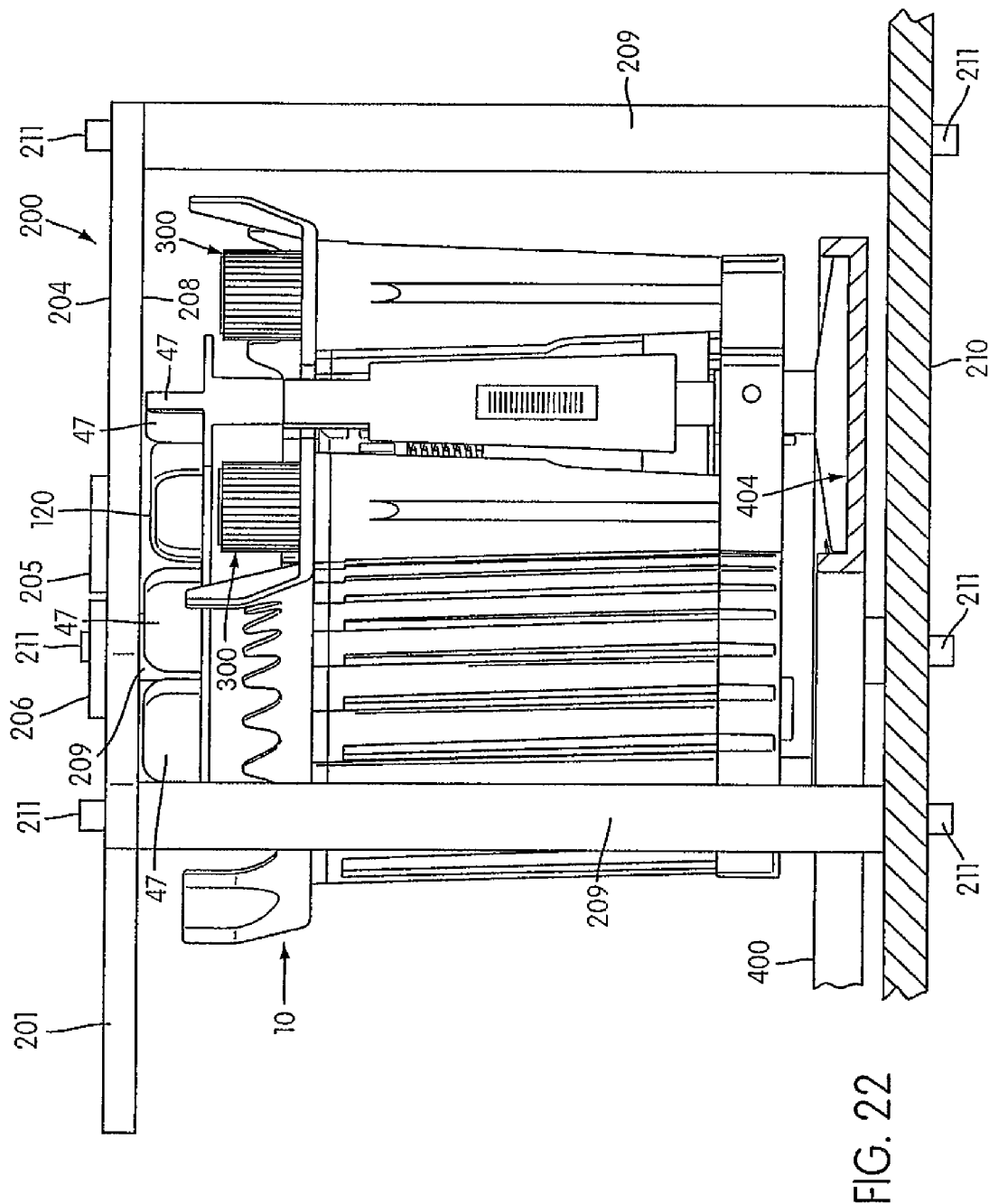
FIG. 22 is an end view of the sample carrier of FIG. 12 being moved under the drip shield of FIG. 19 by the sample carousel of FIG. 18.

When the drip shield 200 is employed in an automated sampling device, the top surface 44 of the top wall 40 preferably includes one or more upwardly extending fins 47, as illustrated in FIGS. 1-3 and 15. The fins 47 are constructed and arranged on the top wall 40 to limit vertical movement of the sample carrier under the drip shield, as illustrated in FIG. 22. Vertical movement of the sample carrier 10 is of particular concern when a robotic pipettor is used to withdraw test sample from sample tubes 300 having penetrable caps 310. Depending on the withdrawal force required, it may be possible for a pipette tip mounted on a robotic pipettor to become snagged on the penetrable components of the cap 310 as the pipette tip is being withdrawn from the sample tube 300. As a consequence, a portion of the sample carrier 10 may be lifted from, and possibly relocated on, the sample carrier conveying means (e.g., sample carousel) by the robotic pipettor. Therefore, to limit vertical movement of the sample carrier 10 under the drip shield 200, the distance between a top surface 48 of the fins 47 and a bottom surface 208 of the drip shield is less than the vertical distance needed to extract or displace at least a portion of the sample carrier from its location on the sample carrier conveying means (e.g., less than the depth of a sample carrier receiving well 404 dimensioned to receive and hold the sample carrier). Preferably, the distance between the top surface 48 of the fins 47 and the bottom surface 208 of the drip shield 200 is no more than about 0.125 inches (3.18 mm). In a preferred embodiment, the sample carrier 10 includes four longitudinally centered fins 47, two on each side of the slot 43. The fins 47 can also function as barriers to carryover contamination between sample tubes 300 held in the opposed sample tube receiving structures 70A, 70B of the preferred sample carrier 10.

The drip shield 200 can be maintained in fixed relationship over sample carriers 10 being indexed on the sample carousel 400 therebelow by means of mounting posts 209 fixed to a stationary surface 210 of the automated sampling system, as illustrated in FIG. 18 and as more fully described by Ammann et al. in U.S. Pat. No. 6,335,166. The drip shield 200 can be secured to these mounting posts 209 using screws, bolts or like mechanical fasteners. Preferred are bolts 211 mated with threaded holes (not shown) in the mounting posts 209 which are inserted through three through-holes 212 located on the periphery of the drip shield 200, as shown in FIGS. 18 and 19.

Sample carriers 10 and drip shields 200 of the present invention are preferably made of a substantially non-conductive plastic, such as acrylonitrile-butadiene-styrene (ABS), which can be obtained from GE Plastics of Pittsfield, Mass. as Cycolac® MG47. The materials used should be selected to resist corrosion by chemicals and reagents that the sample carrier 10 and drip shield 200 may be exposed to during use. The drip shield 200 is preferably a machined component. The components of the preferred sample carrier 10 are preferably formed by injection molding procedures well known to those skilled in the art.

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

What we claim is:

1. A method for obtaining sample material from each of a plurality of sample tubes, the method comprising the steps of:
    a) inserting one or more sample tubes into a sample tube receiving structure of a sample carrier, wherein the sample tube receiving structure is adapted to receive a plurality of sample tubes therein, and wherein each of the sample tubes is received into a different sample tube receiving area of the sample tube receiving structure;
    b) after step a), changing the orientation of the sample tube receiving structure relative to a frame of the sample carrier, thereby subjecting each of the sample tubes to a retaining force; and
    c) withdrawing at least a portion of a sample material from each of the sample tubes, wherein the sample tubes remain in the sample tube receiving areas during the withdrawing step,
    wherein the sample tubes are not subjected to a retaining force prior to step b).

2. The method of claim 1, wherein the sample tube receiving structure is releasably locked relative to a support wall of the frame of the sample carrier during step b).

3. The method of claim 1, wherein the sample tube receiving structure pivots relative to the frame of the sample carrier during step b).

4. The method of claim 3, wherein each of the sample tubes is subjected to a retaining force applied by a spring extending from a support wall of the frame during step b).

5. The method of claim 4, wherein each of the sample tubes is subjected to a retaining force of at least about 3 pounds force during step b).

6. The method of claim 1, wherein the withdrawing step includes penetrating a surface of a cap component of each of the sample tubes with a plastic pipette tip mounted on a robotic pipettor.

7. The method of claim 6 further comprising performing an assay with the sample material obtained from each of the sample tubes during the withdrawing step.

8. The method of claim 7, wherein the assay includes performing a procedure for amplifying a nucleic acid sequence which may be present in the sample material of each of the sample tubes.

9. A method for obtaining sample material from each of a plurality of sample tubes, the method comprising the steps of:
   a) inserting one or more sample tubes into each of a pair of opposed sample tube receiving structures of a sample carrier, wherein each sample tube receiving structure is adapted to receive a plurality of sample tubes therein, and wherein each of the sample tubes is received into a different sample tube receiving area of one of the sample tube receiving structures;
   b) after step a), changing the orientation of the sample tube receiving structures relative to a frame of the sample carrier, thereby subjecting each of the sample tubes to a retaining force; and
   c) withdrawing at least a portion of a sample material from each of the sample tubes, wherein the sample tubes remain in the sample tube receiving areas during the withdrawing step,
   wherein the sample tubes are not subjected to a retaining force prior to step b).

10. The method of claim 9, wherein the sample tube receiving structures are releasably locked relative to a support wall of the frame of the sample carrier during step b).

11. The method of claim 9, wherein the sample tube receiving structures pivot relative to the frame of the sample carrier during step b).

12. The method of claim 11, wherein each of the sample tubes is subjected to a retaining force applied by a spring extending from a support wall of the frame during step b).

13. The method of claim 12, wherein each of the sample tubes is subjected to a retaining force of at least about 3 pounds force during step b).

14. The method of claim 9, wherein the sample carrier has an arcuate shape.

15. The method of claim 9, wherein the withdrawing step includes penetrating a surface of a cap component of each of the sample tubes with a plastic pipette tip mounted on a robotic pipettor.

16. The method of claim 15 further comprising performing an assay with the sample material obtained from each of the sample tubes during the withdrawing step.

17. The method of claim 16, wherein the assay includes performing a procedure for amplifying a nucleic acid sequence which may be present in the sample material of each of the sample tubes.

* * * * *